United States Patent
Brindle et al.

(10) Patent No.: US 10,208,100 B2
(45) Date of Patent: Feb. 19, 2019

(54) ANGIOPOIETIN-2 SPECIFIC TIE2 RECEPTOR

(71) Applicant: United Kingdom Research and Innovation, Swindon (GB)

(72) Inventors: Nicolas Phillip James Brindle, Leicester (GB); Julian Edward Sale, Cambridge (GB)

(73) Assignee: UNITED KINGDOM RESEARCH AND INNOVATION, Swindon (GB)

( * ) Notice: Subject to any disclaimer, the term of this patent is extended or adjusted under 35 U.S.C. 154(b) by 141 days.

(21) Appl. No.: 14/653,734

(22) PCT Filed: Dec. 20, 2013

(86) PCT No.: PCT/GB2013/053392
§ 371 (c)(1),
(2) Date: Jun. 18, 2015

(87) PCT Pub. No.: WO2014/096855
PCT Pub. Date: Jun. 26, 2014

(65) Prior Publication Data
US 2015/0322414 A1    Nov. 12, 2015

(30) Foreign Application Priority Data
Dec. 20, 2012   (GB) .................. 1223053.8

(51) Int. Cl.
| C07K 14/705 | (2006.01) |
| C07K 14/71 | (2006.01) |
| A61K 38/17 | (2006.01) |
| C12N 9/12 | (2006.01) |

(52) U.S. Cl.
CPC ........ *C07K 14/71* (2013.01); *C07K 14/70596* (2013.01); *C12N 9/12* (2013.01); *A61K 38/177* (2013.01); *A61K 38/179* (2013.01); *C07K 14/705* (2013.01); *C12Y 207/10001* (2013.01)

(58) Field of Classification Search
CPC .... A61K 38/00; A61K 38/177; A61K 38/179; C07K 14/00; C07K 14/705; C07K 14/71; C07K 14/70596
See application file for complete search history.

(56) References Cited

U.S. PATENT DOCUMENTS

| 3,773,919 | A |  | 11/1973 | Boswell et al. | |
| 4,376,110 | A |  | 3/1983 | David et al. | |
| 4,485,045 | A |  | 11/1984 | Regen | |
| 4,544,545 | A |  | 10/1985 | Ryan et al. | |
| 5,013,556 | A |  | 5/1991 | Woodle et al. | |
| 6,413,932 | B1 | * | 7/2002 | Cerretti | C07K 14/71 |
| | | | | | 435/69.7 |
| 6,521,424 | B2 | * | 2/2003 | Cerretti | C07K 14/71 |
| | | | | | 435/252.3 |
| 2007/0280947 | A1 | * | 12/2007 | Alitalo | A61K 38/179 |
| | | | | | 424/146.1 |
| 2011/0158978 | A1 | * | 6/2011 | Kirchner | A61K 39/39541 |
| | | | | | 424/130.1 |

FOREIGN PATENT DOCUMENTS

| JP | 2003-501090A A | 1/2003 |
| WO | WO-1991/001753 A1 | 2/1991 |
| WO | WO-2000/022111 A1 | 4/2000 |
| WO | WO-2002/100998 A2 | 12/2002 |
| WO | WO-2003/095636 A2 | 11/2003 |
| WO | WO-2008/132568 A2 | 11/2008 |
| WO | WO-2011014469 A1 | 2/2011 |

OTHER PUBLICATIONS

Bork, A. Powers and pitfalls in sequence analysis: the 70% hurdle. Genome Res 10: 398-400, 2000.*
Bork et al. Go hunting in sequence databases but watch out for the traps. Trends in Genetics. 12(10): 425-427, 1996.*
Brenner, S.E. Errors in genome function. Trends in Genetics 15(4): 132-133, 1999.*
Doerks et al. Protein annotation: detective work for function prediction. Trends in Genetics 14(6): 248-250, 1998.*
Fagiani et al. Angiopoietins in angiogenesis. Cancer Letters 328: 18-26, 2013.*
Ngo et al. Computational complexity, protein structure prediction, and the Levinthal paradox. The Protein Folding Problem and Tertiary Structure Prediction, pp. 492-495, 1994.*
Singh et al. Molecular control of angiopoietin signaling. Biochem Soc Trans 39(6): 1592-1596, 2011.*
Skolnick et al. From genes to protein structure and function: novel applications of computational approaches in the genomic era. Trends in Biotech 18(1): 34-39, 2000.*
Smith et al. The challenges of genome sequence annotation or "The devil is in the details". Nature Biotech 15: 1222-1223, 1997.*
Tokuriki et al. Stability effects of mutations and protein evolvability. Curr Opin Structural Biol 19: 596-604, 2009.*
Wells. J.A. Additivity of mutational effects in proteins. Biochemistry 29 (37): 8509-8517, 1990.*
Alves et al., Imbalances in serum angiopoietin concentrations are early predictors of septic shock development in patients with post chemotherapy febrile neutropenia, *BMC Infect. Dis.*, 10:143 (2010).
Arakawa et al. Protein evolution by hypermutation and selection in the B cell line DT40, *Nucleic Acids Res.*, 36(1):e1 (2008).

(Continued)

*Primary Examiner* — Bridget E Bunner
(74) *Attorney, Agent, or Firm* — Marshall, Gerstein & Borun LLP

(57) ABSTRACT

In one aspect, provided herein is a polypeptide comprising a modified angiopoietin receptor or fragment thereof, wherein the polypeptide binds preferentially to angiopoietin-2 compared to angiopoietin-1. Nucleic acid sequences encoding the polypeptide, as well as pharmaceutical uses of the polypeptide in treating diseases such as cancer and inflammation are also provided.

6 Claims, 27 Drawing Sheets

Specification includes a Sequence Listing.

(56) References Cited

OTHER PUBLICATIONS

Augustin et al., Control of vascular morphogenesis and homeostasis through the angiopoietin-Tie system, *Nat. Rev. Mol. Cell. Biol.*, 10:165-77 (2009).
Barton et al., Crystal structures of the Tie2 receptor ectodomain and the angiopoietin-2-Tie2 complex, *Nat. Struct. Mol. Biol.*, 13:524-32 (2006).
Brindle et al., Directed evolution of an angiopoietin-2 ligand trap by somatic hypermutation and cell surface display, *J. Biol. Chem.*, 288(46):33205-12 (2013).
Brindle et al., Signaling and Functions of Angiopoietin-1 in Vascular Protection, *Circ. Res.*, 98:1014-1023 (2006).
Cumbers et al., Generation and iterative affinity maturation of antibodies in vitro using hypermutating B-cell lines, *Nat. Biotech.*, 20:1129-34 (2002).
Cunningham, et al., High-resolution epitope mapping of hGH-receptor interactions by alanine-scanning mutagenesis, *Science* 244, 1081-1985 (1989).
Daugherty et al., Quantitative analysis of the effect of the mutation frequency on the affinity maturation of single chain Fv antibodies, *Proc. Natl. Acad. Sci. USA*, 97:2029-34 (2000).
David et al., Quantitative analysis of the effect of the mutation frequency on the affinity maturation of single chain Fv antibodies, *Biochemistry*, 13:1014 (1974).
Davis et al., Isolation of angiopoietin-1, a ligand for the TIE2 receptor, by secretion-trap expression cloning, *Cell*, 87:1161-9 (1996).
Dayhoff et al., A model of evolutionary change in proteins. Atlas of protein sequence and structure, *National biomedical research foundation*, 5(Suppl. 3):345-52. (1978).
De Palma et al., Tie2 identifies a hematopoietic lineage of proangiogenic monocytes required for tumor vessel formation and a mesenchymal population of pericyte progenitors, *Cancer Cell*, 8:211-26 (2005).
Dewachter et al., Angiopoietin/Tie2 pathway influences smooth muscle hyperplasia in idiopathic pulmonary hypertension, *Am. J. Respir. Crit. Care Med.*, 174:1025-33 (2006).
Economides et al., Cytokine traps: multi-component, high-affinity blockers of cytokine action, *Nat. Med.*, 9:47-52 (2003).
Eppstein et al., Biological activity of Liposome-encapsulated murine interferon γ is mediated by a cell membrane receptor, *Proc. Natl. Acad. Sci. USA*, 82:3688 (1985).
Felcht et al., Angiopoietin-2 differentially regulates angiogenesis through TIE2 and integrin signaling, *J. Clin. Invest.*, 122:1991-2005 (2012).
Fiedler et al., Angiopoietin-1 and angiopoietin-2 share the same binding domains in the Tie-2 receptor involving the first Ig-like loop and the epidermal growth factor-like repeats, *J. Biol. Chem.*, 278(3):1721-7 (2003).
Fiedler et al., Angiopoietin-2 sensitizes endothelial cells to tnf-alpha and is required for induction of inflammation, *Nat. Med.*, 12:235-9 (2005).
Gonnet et al., Exhaustive matching of the entire pretein sequence database, *Science*, 256:1443 (1992).
Hashimoto et al., Abnormal balance in the angiopoietin-tie2 system in human brain arteriovenous malformations, *Circ. Res.*, 89:111-3 (2001).
Henikoff et al., Amino acid substitution matrices from protein blocks, *Proc. Natl Acad. Sci. USA*, 89:10915 (1992).
Holopainen et al., Effects of Angiopoietin-2-Blocking Antibody on Endothelial Cell-Cell Junctions and Lung Metastasis, *J. Natl. Cancer Inst.*, 104:461-75 (2012).
Huang et al., Targeting the ANGPT-TIE2 pathway in malignancy, *Nat. Rev. Cancer*, 10:575-85. (2010).
Huang, Receptor-Fc fusion therapeutics, traps, and Mimetibody technology, *Curr. Opin. Biotech.*, 20:692-9 (2009).
Hunter et al., Preparation of Iodine-131 Labelled Human Growth Hormone of High Specific Activity, *Nature*, 144:495 (1962).
Hwang et al., Hepatic uptake and degradation of unilamellar sphingomyelin/cholesterol liposomes: a kinetic study, *Proc. Natl. Acad. Sci. USA*, 77:4030 (1980).
Jacket et al., Protein Design by Directed Evolution, *Annu. Rev. Biophys.*, 37:153-73 (2008).
Kim et al., Angiopoietin-2 at high concentration can enhance endothelial cell survival through the phosphatidylinositol 3'-kinase/Akt signal transduction pathway, *Oncogene*, 19:4549-52 (2000).
Koh et al., Double Antiangiogenic Protein, DAAP, Targeting VEGF-A and Angiopoietins in Tumor Angiogenesis, Metastasis, and Vascular Leakage, *Cancer Cell*, 18:171-84 (2010).
Kumpers et al., Angiopoietin-2 in patients requiring renal replacement therapy in the icu: Relation to acute kidney injury, multiple organ dysfunction syndrome and outcome, *Intensive Care Med.*, 36:462-70 (2010).
Langer et al., Biocompatibility of polymeric delivery systems for macromolecules, *J. Biomed. Mater. Res.*, 15:167 (1981).
Langer, Controlled release of macromolecules, *Chem. Tech.*, 12:98-105 (1982).
Macdonald et al., Structure of the extracellular domain of Tie receptor tyrosine kinases and localization of the angiopoietin-binding epitope, *J. Biol. Chem.*, 281:28408-14 (2006).
Maisonpierre et al., Angiopoietin-2, a natural antagonist for Tie2 that disrupts in vivo angiogenesis, *Science*, 277:55-60 (1997).
Mazzieri et al., Targeting the ANG2/TIE2 Axis Inhibits Tumor Growth and Metastasis by Impairing Angiogenesis and Disabling Rebounds of Proangiogenic Myeloid Cells, *Cancer Cell*, 19:512-26 (2011).
Nygren, Hepatic uptake and degradation of unilamellar sphingomyelin/cholesterol liposomes: a kinetic study, *J. Histochem. and Cytochem.*, 30:407 (1982).
Oliner et al., Suppression of angiogenesis and tumor growth by selective inhibition of angiopoietin-2, *Cancer Cell*, 6:507-16 (2004).
Pain et al., Preparation of protein A-peroxidase monoconjugate using a heterobifunctional reagent, and its use in enzyme immunoassays, *J. Immunol. Meth.*, 40:219 (1981).
Parikh et al., Excess circulating angiopoietin—2 may contribute to pulmonary vascular leak in sepsis in humans, *PLoS Med.*, 3(3):e46 (2006).
Rennel et al., A human neutralizing antibody specific to Ang-2 inhibits ocular angiogenesis, *Microcirculation*, 18:598-607 (2011).
Roviezzo et al., Angiopoietin-2 causes inflammation in vivo by promoting vascular leakage, *J. Pharmacol. Exp. Ther.*, 314:738-44 (2005).
Sale et al., Ablation of XRCC2/3 transforms immunoglobulin V gene conversion into somatic hypermutation, *Nature*, 412:921-6 (2001).
Sidman et al., Controlled release of macromolecules and pharmaceuticals from synthetic polypeptides based on glutamic acid, *Biopolymers*, 22:547-56 (1983).
Tabruyn et al., Angiopoietin-2-Driven Vascular Remodeling in Airway Inflammation, *Am. J. Pathol.*, 177:3233-44 (2010).
Thurston et al., The Complex Role of Angiopoietin-2 in the Angiopoietin-Tie Signalling Pathway, *CSHLP Perspectives in Medicine*, 1-13 (2012).
Tracewell et al., Directed enzyme evolution: climbing fitness peaks one amino acid at a time, *Curr. Opin. Chem. Biol.*, 13:3-9 (2009).
UniProtKB/Swiss-Prot database accession No. Q02763 dated Dec. 16, 2008.
Wang et al., Evolution of new nonantibody proteins via iterative somatic hypermutation, *Proc. Natl. Acad. Sci. USA*, 101:16745-9 (2004).
Watson et al., Structure of HDAC3 bound to co-repressor and inositol tetraphosphate, *Nature*, 481:335-40 (2012).
Welford et al., TIE2-expressing macrophages limit the therapeutic efficacy of the vascular-disrupting agent combretastatin A4 phosphate in mice, *J. Clin. Invest.*, 121:1969-73 (2011).
White et al., Inhibition of rat corneal angiogenesis by a nuclease-resistant RNA aptamer specific for angiopoietin-2, *Proc. Nati. Acad. Sci. USA*, 100:5028-33 (2003).
Yuan et al., Angiopoietin 2 Is a Partial Agonist/Antagonist of Tie2 Signaling in the Endothelium, *Mol. Cell. Biol.*, 29:2011-22 (2009).
Ziegler et al., Angiopoietin 2 mediates microvascular and hemodynamic alterations in sepsis, *J. Clin. Invest.*, 123(8):3436-45 (2013).

(56) References Cited

OTHER PUBLICATIONS

International Search Report and Written Opinion of the International Searching Authority, PCT/GB2013/053392, dated Mar. 18, 2014.
Japanese Search Report of Office Action issued in connection with JP2015-548770 and its machine translation, dated Oct. 16, 2017.

* cited by examiner

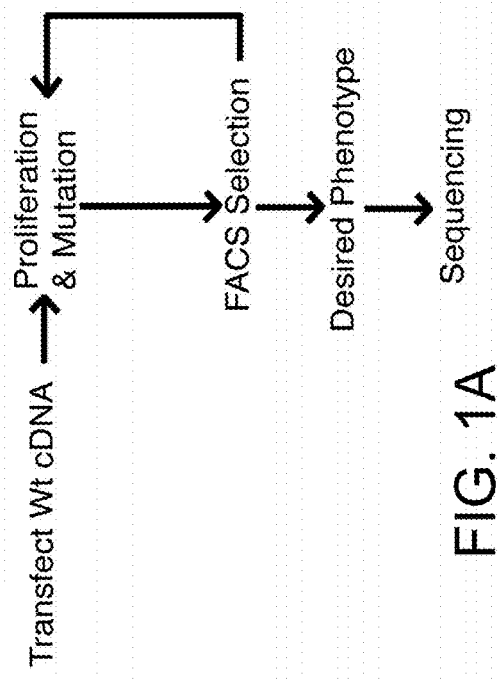

Anti- FLAG

1    MDSLASLVLCGVSLLLSGTVEGAMDLILINSLPLVSDAETSLTCIASGWR
51   PHEPITIGRDFEALMNQHQDPLEVTQDVTREWAKKVVWKREKASKINGAY
101  FCEGRVRGEAIRIRTMKMRQQASFLPATLTMTVDKGDNVNISFKKVLIKE
151  EDAVIYKNGS IHSVP  EVPDILEVHLPHAQPQDAGVYSARYIGGNLFT
201  SAFTRLIVRRCEAQKWGPECNHLCTACMNNGVCHEDTGECICPPGFMGRT
251  CEKACELHTFGRTCKERCSGQEGCKSYVFCLPDPYGCSCATGWKGLQCNE
301  ACHPGFYGPDCKLRCSCNNGEMCDRFQGCLCSPGWQGLQCEREGIPRMTP
351  KIVDLPDHIEVNSGKFNPICKASGWPLPTNEEMTLVKPDGTVLHPKDFNH
401  TDHFSVAIFTIHRILPPDSGVWVCSVNTVAGMVEKPFNISVK

FIG. 3A

| | |
|---|---|
| 1 | ATGGACTCTTTAGCCAGCTTAGTTCTCTGTGGAGTCAGCTTGCTCCTTTC |
| 51 | TGGAACTGTGGAAGGTGCCATGGACTTGATCTTGATCAATTCCCTACCTC |
| 101 | TTGTATCTGATGCTGAAACATCTCTCACCTGCATTGCTCTGGGTGGCGC |
| 151 | CCCCATGAGCCCATCACCATAGAAGGGACTTTGAAGCCTTAATGAACCA |
| 201 | GCACCAGGATCCGCTGGAAGTTACTCAAGATGTGACCAGAGAATGGGCTA |
| 251 | AAAAGTTGTTTGGAAGAGAGAAAGGCTAGTAAGATCAATGGTGCTTAT |
| 301 | TTCTGTGAAGGGCGAGTTCGAGGAGAGGCAATCAGGATACGAACCATGAA |
| 351 | GATGCGTCAACAAGCTTCCTTCCTACCAGCTACTTTAACTATGACTGTGG |
| 401 | ACAAGGGAGATAACGTGAACATATCTTTCAAAAGGTATTGATTAAAGAA |
| 451 | GAAGATGCAGTGATTTACAAAAATGGTTCCTTCATCCATTCAGTGCCCCG |
| 501 | GCATGAAGTACCTGATATTCTAGAAGTACACCTGCCTCATGCTCAGCCCC |
| 551 | AGGATGCTGGAGTGTACTCGGCCAGGTATATAGGAGGAAACCTCTTCACC |
| 601 | TCGGCCTTCACCAGGCTGATAGTCCGGAGATGTGAAGCCCAGAAGTGGGG |
| 651 | ACCTGAATGCAACCATCTCTGTACTGCTTGTATGAACAATGGTGTCTGCC |

FIG. 9A

```
701  ATGAAGATACTGGAGAATGCATTTGCCCTCCTGGGTTTATGGGAAGGACG

751  TGTGAGAAGGCTTGTGAACTGCACACGTTTGGCAGAACTTGTAAAGAAAG

801  GTGCAGTGGACAAGAGGGATGCAAGTCTTATGTGTTCTGTCTCCTGACC

851  CCTATGGGTGTTCCTGTGCCACAGGCTGGAAGGGTCTGCAGTGCAATGAA
                                                    G
901  GCATGCCACCCTGGTTTTACGGGCCAGATTGTAAGCTTAGGTGCAGCTG

951  CAACAATGGGGAGATGTGTGATCGCTTCCAAGGATGTCTCTGCTCTCCAG
                              A
1001 GATGGCAGGGGCTCCAGTGTGAGAGAGAAGGCATACCGAGGATGACCCCA

1051 AAGATAGTGGATTTGCCAGATCATATAGAAGTAAACAGTGGTAAATTTAA

1101 TCCCATTTGCAAAGCTTCTGGCTGGCCGCTACCTACTAATGAAGAAATGA
              A         G
1151 CCCTGGTGAAGCCGGATGGGACAGTGCTCCATCCAAAAGACTTTAACCAT

1201 ACGGATCATTTCTCAGTAGCCATATTCACCATCCACCGGATCCTCCCCCC
                        A
1251 TGACTCAGGAGTTTGGGTCTGCAGTGTGAACACAGTGGCTGGGATGGTGG

1301 AAAAGCCCTTCAACATTTCTGTTAA
```

FIG. 9B

```
401  ACAAGGGAGATAACGTGAACATATCTTTCAAAAAGGTATTGATTAAAGAA
                C                        A              ----
451  GAAGATGCAGTGATTTACAAAAATGGTTCCTTCATCCATTCAGTGCCCCG
          ----   TA  G
501  GCATGAAGTACCTGATATTCTAGAAGTACACCTGCCTCATGCTCAGCCCC

551  AGGATGCTGGAGTGTACTCGGCCAGGTATATAGGAGGAAACCTCTTCACC

601  TCGGCCTTCACCAGGCTGATAGTCCGGAGATGTGAAGCCCAGAAGTGGGG
                                  S
651  ACCTGAATGCAACCATCTCTGTACTGCTTGTATGAACAATGGTGTCTGCC

701  ATGAAGATACTGGAGAATGCATTTGCCCTCCTGGGTTTATGGGAAGGACG
```

FIG. 10A

```
101  FCEGRVRGEAIRIRTMKMRQQASFLPATLTMTVDKGDNVNISFKKVLIKE
          L       I     --DIA
151  EDAVIYKNGSFIHSVPRHEVFDILEVHLPHAQPQDAGVYSARYIGGNLFT
                                  S
201  SAFTRLIVRRCEAQKWGPECNHLCTACMNNGVCHEDTGECICFPGFMGRT

251  CEKACELHTFGRTCKERCSGQEGCKSYVFCLPDPYGCSATGWKGLQCNE
```

FIG. 10B

```
         10         20         30         40         50         60
MDSLASLVLC GVSLLLSGTV EGAMDLILIN SLPLVSDAET SLTCIASGWR PHEPITIGRD 70         80         90        100        110        120
FEALMNQHQD PLEVTQDVTR EWAKKVVWKR EKASKINGAY FCEGRVRGEA IRIRTMKMRQ 130        140        150        160        170        180
QASFLPATLT MTVDKGDNVN ISFKKVLIKE EDAVIYKNGS FIHSVPRHEV PDILEVHLPH 190        200        210        220        230        240
AQPQDAGVYS ARYIGGNLFT SAFTRLIVRR CEAQKWGPEC NHLCTACMNN GVCHEDTGEC 250        260        270        280        290        300
ICPPGFMGRT CEKACELHTF GRTCKERCSG QEGCKSYVFC LPDPYGCSCA TGWKGLQCNE 310        320        330        340        350        360
ACHPGFYGPD CKLRCSCNNG EMCDRFQGCL CSPGWQGLQC EREGIQRMTP KIVDLPDHIE
```

FIG. 12A

```
       370        380        390        400        410        420
VNSGKFNPIC KASGWPLPTN EEMTLVKPDG TVLHPKDFNH TDHFSVAIFT IHRILPPDSG 430        440        450        460        470        480
VWVCSVNTVA GMVEKPFNIS VKVLPKPLNA PNVIDTGHNF AVINISSEPY FGDGPIKSKK 490        500        510        520        530        540
LLYKPVNHYE AWQHIQVTNE IVTLNYLEPR TEYELCVQLV RRGEGGEGHP GPVRRFTTAS 550        560        570        580        590        600
IGLPPPRGLN LLPKSQTTLN LTWQPIFPSS EDDFYVEVER RSVQKSDQQN IKVPGNLTSV 610        620        630        640        650        660
LLNNLHPREQ YVVRARVNTK AQGEWSEDLT AWTLSDILPP QPENIKISNI THSSAVISWT 670        680        690        700        710        720
ILDGYSISSI TIRYKVQGKN EDQHVDVKIK NATITQYQLK GLEPETAYQV DIFAENNIGS 730        740        750        760        770        780
SNPAFSHELV TLPESQAPAD LGGGKMLLIA ILGSAGMTCL TVLLAFLIIL QLKRANVQRR
```

FIG. 12B

```
        790        800        810        820        830        840
MAQAFQNVRE EPAVQFNSGT LALNRKVKNN PDPTIYPVLD WNDIKFQDVI GEGNFGQVLK 850        860        870        880        890        900
ARIKKDGLRM DAAIKRMKEY ASKDDHRDFA GELEVLCKLG HHPNIINLLG ACEHRGYLYL 910        920        930        940        950        960
AIEYAPHGNL LDFLRKSRVL ETDPAFAIAN STASTLSSQQ LLHFAADVAR GMDYLSQKQF 970        980        990       1000       1010       1020
IHRDLAARNI LVGENYVAKI ADFGLSRGQE VYVKKTMGRL PVRWMAIESL NYSVYTTNSD 1030       1040       1050       1060       1070       1080
VWSYGVLLWE IVSLGGTPYC GMTCAELYEK LPQGYRLEKP LNCDDEVYDL MRQCWREKPY 1090       1100       1110       1120
ERPSFAQILV SLNRMLEERK TYVNTTLYEK FTYAGIDCSA EEAA
```

FIG. 12C

SEQUENCE LISTING

```
<160> NUMBER OF SEQ ID NOS: 11

<210> SEQ ID NO 1
<211> LENGTH: 1124
<212> TYPE: PRT
<213> ORGANISM: Homo sapiens

<400> SEQUENCE: 1

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255
```

```
Leu His Thr Phe Gly Arg Thr Cys Lys Glu Arg Cys Ser Gln Glu
                260                 265                 270

Gly Cys Lys Ser Tyr Val Phe Cys Leu Pro Asp Pro Tyr Gly Cys Ser
            275                 280                 285

Cys Ala Thr Gly Trp Lys Gly Leu Gln Cys Asn Glu Ala Cys His Pro
    290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Gln Arg Met Thr Pro Lys Ile
            340                 345                 350

Val Asp Leu Pro Asp His Ile Glu Val Asn Ser Gly Lys Phe Asn Pro
                355                 360                 365

Ile Cys Lys Ala Ser Gly Trp Pro Leu Pro Thr Asn Glu Glu Met Thr
370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
                420                 425                 430

Val Glu Lys Pro Phe Asn Ile Ser Val Lys Val Leu Pro Lys Pro Leu
            435                 440                 445

Asn Ala Pro Asn Val Ile Asp Thr Gly His Asn Phe Ala Val Ile Asn
450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
            515                 520                 525

His Pro Gly Pro Val Arg Arg Phe Thr Thr Ala Ser Ile Gly Leu Pro
    530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Gln Asn Ile Lys
            580                 585                 590

Val Pro Gly Asn Leu Thr Ser Val Leu Leu Asn Asn Leu His Pro Arg
    595                 600                 605

Glu Gln Tyr Val Val Arg Ala Arg Val Asn Thr Lys Ala Gln Gly Glu
    610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ser Ile Thr Ile
            660                 665                 670

Arg Tyr Lys Val Gln Gly Lys Asn Glu Asp Gln His Val Asp Val Lys
```

```
              675             680             685
Ile Lys Asn Ala Thr Ile Thr Gln Tyr Gln Leu Lys Gly Leu Glu Pro
    690                 695                 700
Glu Thr Ala Tyr Gln Val Asp Ile Phe Ala Glu Asn Asn Ile Gly Ser
705                 710                 715                 720
Ser Asn Pro Ala Phe Ser His Glu Leu Val Thr Leu Pro Glu Ser Gln
                725                 730                 735
Ala Pro Ala Asp Leu Gly Gly Lys Met Leu Leu Ile Ala Ile Leu
            740                 745                 750
Gly Ser Ala Gly Met Thr Cys Leu Thr Val Leu Leu Ala Phe Leu Ile
        755                 760                 765
Ile Leu Gln Leu Lys Arg Ala Asn Val Gln Arg Arg Met Ala Gln Ala
770                 775                 780
Phe Gln Asn Val Arg Glu Glu Pro Ala Val Gln Phe Asn Ser Gly Thr
785                 790                 795                 800
Leu Ala Leu Asn Arg Lys Val Lys Asn Asn Pro Asp Pro Thr Ile Tyr
                805                 810                 815
Pro Val Leu Asp Trp Asn Asp Ile Lys Phe Gln Asp Val Ile Gly Glu
            820                 825                 830
Gly Asn Phe Gly Gln Val Leu Lys Ala Arg Ile Lys Lys Asp Gly Leu
        835                 840                 845
Arg Met Asp Ala Ala Ile Lys Arg Met Lys Glu Tyr Ala Ser Lys Asp
850                 855                 860
Asp His Arg Asp Phe Ala Gly Glu Leu Glu Val Leu Cys Lys Leu Gly
865                 870                 875                 880
His His Pro Asn Ile Ile Asn Leu Leu Gly Ala Cys Glu His Arg Gly
                885                 890                 895
Tyr Leu Tyr Leu Ala Ile Glu Tyr Ala Pro His Gly Asn Leu Leu Asp
            900                 905                 910
Phe Leu Arg Lys Ser Arg Val Leu Glu Thr Asp Pro Ala Phe Ala Ile
        915                 920                 925
Ala Asn Ser Thr Ala Ser Thr Leu Ser Ser Gln Gln Leu Leu His Phe
930                 935                 940
Ala Ala Asp Val Ala Arg Gly Met Asp Tyr Leu Ser Gln Lys Gln Phe
945                 950                 955                 960
Ile His Arg Asp Leu Ala Ala Arg Asn Ile Leu Val Gly Glu Asn Tyr
                965                 970                 975
Val Ala Lys Ile Ala Asp Phe Gly Leu Ser Arg Gly Gln Glu Val Tyr
            980                 985                 990
Val Lys Lys Thr Met Gly Arg Leu Pro Val Arg Trp Met Ala Ile Glu
        995                 1000                1005
Ser Leu Asn Tyr Ser Val Tyr Thr Thr Asn Ser Asp Val Trp Ser
    1010                1015                1020
Tyr Gly Val Leu Leu Trp Glu Ile Val Ser Leu Gly Gly Thr Pro
    1025                1030                1035
Tyr Cys Gly Met Thr Cys Ala Glu Leu Tyr Glu Lys Leu Pro Gln
    1040                1045                1050
Gly Tyr Arg Leu Glu Lys Pro Leu Asn Cys Asp Asp Glu Val Tyr
    1055                1060                1065
Asp Leu Met Arg Gln Cys Trp Arg Glu Lys Pro Tyr Glu Arg Pro
    1070                1075                1080
Ser Phe Ala Gln Ile Leu Val Ser Leu Asn Arg Met Leu Glu Glu
    1085                1090                1095
```

Arg Lys Thr Tyr Val Asn Thr Thr Leu Tyr Glu Lys Phe Thr Tyr
1100            1105                1110

Ala Gly Ile Asp Cys Ser Ala Glu Glu Ala Ala
    1115                1120

<210> SEQ ID NO 2
<211> LENGTH: 442
<212> TYPE: PRT
<213> ORGANISM: Homo sapiens

<400> SEQUENCE: 2

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Gln Arg Met Thr Pro Lys Ile

```
                340             345             350
Val Asp Leu Pro Asp His Ile Glu Val Asn Ser Gly Lys Phe Asn Pro
            355                 360                 365

Ile Cys Lys Ala Ser Gly Trp Pro Leu Pro Thr Asn Glu Glu Met Thr
        370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
            405                 410                 415

Pro Asp Ser Gly Val Trp Val Cys Ser Val Asn Thr Val Ala Gly Met
        420                 425                 430

Val Glu Lys Pro Phe Asn Ile Ser Val Lys
        435                 440

<210> SEQ ID NO 3
<211> LENGTH: 440
<212> TYPE: PRT
<213> ORGANISM: Artificial Sequence
<220> FEATURE:
<223> OTHER INFORMATION: Modified sequence of human Tie2

<400> SEQUENCE: 3

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Ile Ile His Ser Val Pro Glu Val Pro Asp Ile Leu Glu Val His Leu
                165                 170                 175

Pro His Ala Gln Pro Gln Asp Ala Gly Val Tyr Ser Ala Arg Tyr Ile
            180                 185                 190

Gly Gly Asn Leu Phe Thr Ser Ala Phe Thr Arg Leu Ile Val Arg Arg
        195                 200                 205

Cys Glu Ala Gln Lys Trp Gly Pro Glu Cys Asn His Leu Cys Thr Ala
    210                 215                 220

Cys Met Asn Asn Gly Val Cys His Glu Asp Thr Gly Glu Cys Ile Cys
225                 230                 235                 240

Pro Pro Gly Phe Met Gly Arg Thr Cys Glu Lys Ala Cys Glu Leu His
                245                 250                 255

Thr Phe Gly Arg Thr Cys Lys Glu Arg Cys Ser Gly Gln Glu Gly Cys
```

```
                260                 265                 270
Lys Ser Tyr Val Phe Cys Leu Pro Asp Pro Tyr Gly Cys Ser Cys Ala
            275                 280                 285

Thr Gly Trp Lys Gly Leu Gln Cys Asn Glu Ala Cys His Pro Gly Phe
        290                 295                 300

Tyr Gly Pro Asp Cys Lys Leu Arg Cys Ser Cys Asn Asn Gly Glu Met
305                 310                 315                 320

Cys Asp Arg Phe Gln Gly Cys Leu Cys Ser Pro Gly Trp Gln Gly Leu
                325                 330                 335

Gln Cys Glu Arg Glu Gly Ile Gln Arg Met Thr Pro Lys Ile Val Asp
            340                 345                 350

Leu Pro Asp His Ile Glu Val Asn Ser Gly Lys Phe Asn Pro Ile Cys
        355                 360                 365

Lys Ala Ser Gly Trp Pro Leu Pro Thr Asn Glu Met Thr Leu Val
    370                 375                 380

Lys Pro Asp Gly Thr Val Leu His Pro Lys Asp Phe Asn His Thr Asp
385                 390                 395                 400

His Phe Ser Val Ala Ile Phe Thr Ile His Arg Ile Leu Pro Pro Asp
                405                 410                 415

Ser Gly Val Trp Val Cys Ser Val Asn Thr Val Ala Gly Met Val Glu
            420                 425                 430

Lys Pro Phe Asn Ile Ser Val Lys
        435                 440

<210> SEQ ID NO 4
<211> LENGTH: 1325
<212> TYPE: DNA
<213> ORGANISM: Homo sapiens

<400> SEQUENCE: 4
atggactctt tagccagctt agttctctgt ggagtcagct tgctcctttc tggaactgtg      60
gaaggtgcca tggacttgat cttgatcaat tccctacctc ttgtatctga tgctgaaaca     120
tctctcacct gcattgcctc tgggtggcgc cccatgagc ccatcaccat aggaagggac      180
tttgaagcct aatgaaccag caccaggat ccgctggaag ttactcaaga gtgaccaga      240
gaatgggcta aaaagttgtt ttggaagaga gaaaaggcta gtaagatcaa tggtgcttat     300
ttctgtgaag gcgagttcg aggagaggca atcaggatac gaaccatgaa gatgcgtcaa     360
caagcttcct cctaccagc tactttaact atgactgtgg acaagggaga taacgtgaac     420
atatctttca aaaaggtatt gattaaagaa gaagatgcag tgatttacaa aaatggttcc     480
ttcatccatt cagtgccccg gcatgaagta cctgatattc tagaagtaca cctgcctcat     540
gctcagcccc aggatgctgg agtgtactcg gccaggtata taggaggaaa cctcttcacc     600
tcggccttca ccaggctgat agtccggaga tgtgaagccc agaagtgggg acctgaatgc     660
aaccatctct gtactgcttg tatgaacaat ggtgtctgcc atgaagatac tggagaatgc     720
atttgccctc tgggtttat gggaaggacg tgtgagaagg cttgtgaact gcacacgttt     780
ggcagaactt gtaaagaaag gtgcagtgga caagagggat gcaagtctta tgtgttctgt     840
ctccctgacc cctatgggtg ttcctgtgcc acaggctgga agggtctgca gtgcaatgaa     900
gcatgccacc ctggtttta cgggccagat tgtaagctta ggtgcagctg caacaatggg     960
gagatgtgtg atcgcttcca aggatgtctc tgctctccag atggcagggg ctccagtgt    1020
gagagagaag catacccgag gatgacccca aagatagtgg atttgccaga tcatatagaa    1080
```

```
gtaaacagtg gtaaatttaa tcccatttgc aaagcttctg gctggccgct acctactaat      1140
gaagaaatga ccctggtgaa gccggatggg acagtgctcc atccaaaaga ctttaaccat      1200
acggatcatt tctcagtagc catattcacc atccaccgga tcctcccccc tgactcagga      1260
gtttgggtct gcagtgtgaa cacagtggct gggatggtgg aaaagccctt caacatttct      1320
gttaa                                                                 1325

<210> SEQ ID NO 5
<211> LENGTH: 350
<212> TYPE: DNA
<213> ORGANISM: Homo sapiens

<400> SEQUENCE: 5
acaagggaga taacgtgaac atatctttca aaaggtatt gattaaagaa gaagatgcag         60
tgatttacaa aaatggttcc ttcatccatt cagtgccccg gcatgaagta cctgatattc       120
tagaagtaca cctgcctcat gctcagcccc aggatgctgg agtgtactcg gccaggtata       180
taggaggaaa cctcttcacc tcggccttca ccaggctgat agtccggaga gtgaagccc        240 agaagtgggg acctgaatgc aaccatctct gtactgcttg tatgaacaat ggtgtctgcc       300
atgaagatac tggagaatgc atttgccctc ctgggttat gggaaggacg                  350

<210> SEQ ID NO 6
<211> LENGTH: 200
<212> TYPE: PRT
<213> ORGANISM: Homo sapiens

<400> SEQUENCE: 6

Phe Cys Glu Gly Arg Val Arg Gly Glu Ala Ile Arg Ile Arg Thr Met
 1               5                   10                  15

Lys Met Arg Gln Gln Ala Ser Phe Leu Pro Ala Thr Leu Thr Met Thr
            20                  25                  30

Val Asp Lys Gly Asp Asn Val Asn Ile Ser Phe Lys Lys Val Leu Ile
        35                  40                  45

Lys Glu Glu Asp Ala Val Ile Tyr Lys Asn Gly Ser Phe Ile His Ser
    50                  55                  60

Val Pro Arg His Glu Val Pro Asp Ile Leu Glu Val His Leu Pro His
65                  70                  75                  80

Ala Gln Pro Gln Asp Ala Gly Val Tyr Ser Ala Arg Tyr Ile Gly Gly
                85                  90                  95

Asn Leu Phe Thr Ser Ala Phe Thr Arg Leu Ile Val Arg Arg Cys Glu
            100                 105                 110

Ala Gln Lys Trp Gly Pro Glu Cys Asn His Leu Cys Thr Ala Cys Met
        115                 120                 125

Asn Asn Gly Val Cys His Glu Asp Thr Gly Glu Cys Ile Cys Pro Pro
    130                 135                 140

Gly Phe Met Gly Arg Thr Cys Glu Lys Ala Cys Glu Leu His Thr Phe
145                 150                 155                 160

Gly Arg Thr Cys Lys Glu Arg Cys Ser Gly Gln Glu Gly Cys Lys Ser
                165                 170                 175

Tyr Val Phe Cys Leu Pro Asp Pro Tyr Gly Cys Ser Cys Ala Thr Gly
            180                 185                 190

Trp Lys Gly Leu Gln Cys Asn Glu
        195                 200

<210> SEQ ID NO 7
```

```
<211> LENGTH: 75
<212> TYPE: PRT
<213> ORGANISM: Homo sapiens

<400> SEQUENCE: 7

Ala Gly Lys Gln Ser Ser Leu Ile Leu His Gly Ala Asp Phe Ser Thr
1               5                   10                  15
Lys Asp Ala Asp Asn Asp Asn Cys Met Cys Lys Cys Ala Leu Met Leu
            20                  25                  30
Thr Gly Gly Trp Trp Phe Asp Ala Cys Gly Pro Ser Asn Leu Asn Gly
        35                  40                  45
Met Phe Tyr Thr Ala Gly Gln Asn His Gly Lys Leu Asn Gly Ile Lys
    50                  55                  60
Trp His Tyr Phe Lys Gly Pro Ser Tyr Ser Leu
65                  70                  75

<210> SEQ ID NO 8
<211> LENGTH: 75
<212> TYPE: PRT
<213> ORGANISM: Homo sapiens

<400> SEQUENCE: 8

Ala Gly Lys Ile Ser Ser Ile Ser Gln Pro Gly Asn Asp Phe Ser Thr
1               5                   10                  15
Lys Asn Asp Gly Asn Asp Lys Cys Ile Cys Lys Cys Ser Gln Met Leu
            20                  25                  30
Thr Gly Gly Trp Trp Phe Asp Ala Cys Gly Pro Ser Asn Leu Asn Gly
        35                  40                  45
Met Tyr Tyr Pro Gln Arg Gln Asn Thr Asn Lys Phe Asn Gly Ile Lys
    50                  55                  60
Trp Tyr Tyr Trp Lys Gly Ser Gly Tyr Ser Leu
65                  70                  75

<210> SEQ ID NO 9
<211> LENGTH: 1306
<212> TYPE: DNA
<213> ORGANISM: Artificial Sequence
<220> FEATURE:
<223> OTHER INFORMATION: Modified sequence of human Tie2

<400> SEQUENCE: 9
atggactctt tagccagctt agttctctgt ggagtcagct tgctcctttc tggaactgtg      60
gaaggtgcca tggacttgat cttgatcaat tccctacctc ttgtatctga tgctgaaaca     120
tctctcacct gcattgtctc tgggtggcgc cccatgagc ccatcaccat agaagggact     180
ttgaagcctt aatgaaccag caccaggatc cgctggaagt tactcaagat gtgaccagag     240
aatgggctaa aaagttgtt tggaagagag aaaaggctag taagatcaat ggtgcttatt     300
tctgtgaagg gcgagttcga ggagaggcaa tcaggatacg aaccatgaag atgcgtcaac     360
aagcttcctt cctaccagct actttaacta tgactgtgga caaggagat aacgtgaaca     420
tatctttcaa aaaggtattg attaaagaag aagatgcagt gatttacaaa aatggttcct     480
tcatccattc agtgccccgg catgaagtac ctgatattct agaagtaacc tgcctcatgg     540
tcagccccag gatgctggag tgtagtcggc aggtatata ggaggaaacc tcttcacctc     600
ggccttcacc aggctgatag tccggagatg tgaagcccag aagtggggac ctgaatgcaa     660
ccatctctgt agtgcttgta tgaacaatgg tgtctgccat gaagatactg gagaatgcat     720
ttgccctcct gggtttatgg gaaggacgtg tgagaaggct tgtgaactgc acacgttt gg     780
```

```
cagaacttgt aaagaaaggt gcagtggaca agaggttctg tctccctgac ccctatgggt    840
gttcctgtgc cacaggctgg aagggtctgc agtgcaatga agcatgccac cctggttttt    900
acgggccaga ttgtaagctt aggtgcaggt gcaacaatgg ggagatgtgt gatcgcttcc    960
aaggatgtct ctgctctcca ggatggcagg ggctccagtg tgagagagaa acataccga   1020 ggatgacccc aaagatagtg gatttgccag atcatataga agtaaacagt ggtaaattta   1080
atcccatttg caaagcttct ggctggccgc tacctactaa tgaagaaatg accctggtga   1140
agccagatgg gacagtggtc catccaaaag actttaacca tacggatcat ttctcagtag   1200
ccatattcac catccaccgg atcctccccc ctgactcagg agtttgggtc tacagtgtga   1260
acacagtggc tgggatggtg gaaaagccct tcaacatttc tgttaa               1306

<210> SEQ ID NO 10
<211> LENGTH: 344
<212> TYPE: DNA
<213> ORGANISM: Artificial Sequence
<220> FEATURE:
<223> OTHER INFORMATION: Modified sequence of human Tie2

<400> SEQUENCE: 10
acaagggaga taacgtgaac atatctttca aaaaggtatt gattaaagaa gaagatgcac     60
tgatttacaa aaatggttcc atcatccatt cagtgcctga tatagctgat attctagaag    120
tacacctgcc tcatgctcag ccccaggatg ctggagtgta ctcggccagg tatataggag    180
gaaacctctt cacctcggcc ttcaccaggc tgatagtccg gagatgtgaa gcccagaagt    240
ggggacctga atgcaaccat ctctgtagtg cttgtatgaa caatggtgtc tgccatgaag    300
atactggaga atgcatttgc cctcctgggt ttatgggaag gacg                    344

<210> SEQ ID NO 11
<211> LENGTH: 198
<212> TYPE: PRT
<213> ORGANISM: Artificial Sequence
<220> FEATURE:
<223> OTHER INFORMATION: Modified sequence of human Tie2

<400> SEQUENCE: 11

Phe Cys Glu Gly Arg Val Arg Gly Glu Ala Ile Arg Ile Arg Thr Met
1               5                  10                  15

Lys Met Arg Gln Gln Ala Ser Phe Leu Pro Ala Thr Leu Thr Met Thr
            20                  25                  30

Val Asp Lys Gly Asp Asn Val Asn Ile Ser Phe Lys Lys Val Leu Ile
        35                  40                  45

Lys Glu Glu Asp Ala Leu Ile Tyr Lys Asn Gly Ser Ile Ile His Ser
    50                  55                  60

Val Pro Asp Ile Ala Asp Ile Leu Glu Val His Leu Pro His Ala Gln
65                  70                  75                  80

Pro Gln Asp Ala Gly Val Tyr Ser Ala Arg Tyr Ile Gly Gly Asn Leu
                85                  90                  95

Phe Thr Ser Ala Phe Thr Arg Leu Ile Val Arg Arg Cys Glu Ala Gln
            100                 105                 110

Lys Trp Gly Pro Glu Cys Asn His Leu Cys Ser Ala Cys Met Asn Asn
        115                 120                 125

Gly Val Cys His Glu Asp Thr Gly Glu Cys Ile Cys Pro Pro Gly Phe
    130                 135                 140

Met Gly Arg Thr Cys Glu Lys Ala Cys Glu Leu His Thr Phe Gly Arg
```

```
145                 150                 155                 160
Thr Cys Lys Glu Arg Cys Ser Gly Gln Glu Gly Cys Lys Ser Tyr Val
                165                 170                 175
Phe Cys Leu Pro Asp Pro Tyr Gly Cys Ser Cys Ala Thr Gly Trp Lys
                180                 185                 190
Gly Leu Gln Cys Asn Glu
            195
```

ANGIOPOIETIN-2 SPECIFIC TIE2 RECEPTOR

FIELD

The present invention relates to polypeptides useful for treating diseases in humans and animals. In particular, the invention relates to polypeptide inhibitors of angiopoietin-2 and their use in treating diseases such as cancer.

BACKGROUND

Angiopoietin-2 (Ang2) is a 70 kDa secreted ligand whose increased expression has been implicated in a range of diseases, including cancer, sepsis and adult respiratory distress syndrome (1, 2). The primary receptor for Ang2 is the transmembrane tyrosine kinase Tie2 (3) that is expressed mainly on vascular endothelial cells and myeloid cells (1, 4). Ang2 plays an important role in vascular remodeling during development but in adult tissues Ang2 concentrations are usually low. An increase in Ang2 levels in disease allows the molecule to compete for binding to a common interface on Tie2 with the related agonist Ang1 (3). Ang1 is a protective protein constitutively produced by perivascular cells which maintains blood vessel function and quiescence by suppressing inflammation, vessel leakage and endothelial apoptosis (1, 5). Antagonism of Ang1 by Ang2 blocks the proquiescent effects of Ang1 and contributes to Ang2-induced vessel remodelling, inflammation, leakage and oedema. In addition to its actions on endothelial Tie2, Ang2 has a number of other effects relevant to disease. For example, the ligand has recently been shown to bind and activate endothelial integrins to promote sprouting angiogenesis (6), and Ang2 acts on tumour infiltrating Tie2-expressing monocytes to promote tumourigenesis (7, 8).

Because of its involvement in multiple disease processes there have been considerable efforts to develop inhibitors of Ang2, including antibodies and aptamers (9-11). Results from studies with these and related molecules have been encouraging, with reports of Ang2 inhibitors promoting tumor regression and suppressing of metastatic disease in cancer, and decreasing leukocyte infiltration and vascular remodeling in airway inflammation (7, 10, 12, 13).

A complementary approach to the use of antibodies for blocking pathological levels of ligands is the cytokine or ligand trap (14). These molecules are formed from receptor ectodomain fragments, usually administered as soluble fusion proteins, which sequester the target ligand. Examples of ligand traps in clinical use include Etanercept, a soluble form of tumour necrosis factor-α receptor and Aflibercept, a chimeric fusion protein of fragments of vascular endothelial growth factor receptor-1 and -2 (15). There are significant advantages to ligand traps. Usually they are smaller and have better tissue penetration than antibodies, they already recognize the biologically active part of the target and generally do not require protection from the immune system. A ligand trap specific for Ang2 would be an attractive therapeutic. However the natural receptor for Ang2, Tie2, binds to the protective ligand Ang1 equally well or even better than it does to Ang2 (3, 16, 17).

One of the most effective strategies for engineering new protein functionality is directed protein evolution (18, 19). This process essentially recapitulates the selection and accumulation of desirable mutations that occurs in natural evolution over millions of years, but over a period of weeks in the laboratory. Directed evolution involves repeated rounds of library construction, usually in vitro, expression of the mutant forms of the target protein and selection. Unfortunately this iterative approach to in vitro generation and searching of sequence space is frequently both difficult and labour intensive. B cell lines that constitutively diversify their immunoglobulin variable (IgV) regions by somatic hypermutation (SHM) (20) allow for coupling of diversification and selection of novel antibody specificities. The genetic variation within the Ig genes, introduced by the action of activation induced deaminase (AID) is coupled to the selectable expression of surface Ig on individual cells (21). More recently such cell lines have been used to evolve variants of exogenously expressed green fluorescent protein (22, 23). However, in theory this strategy has enormous potential for directed evolution of a wide range of proteins if the desired phenotype can be selected for in B lines.

There is thus still a need for an improved inhibitor of Ang2. In particular, there is a need for a polypeptide angiopoietin inhibitor which is capable of discriminating between Ang2 and Ang1.

SUMMARY

In one aspect the present invention provides a polypeptide comprising a modified angiopoietin receptor or fragment thereof, wherein the polypeptide binds preferentially to angiopoietin-2 compared to angiopoietin-1.

In one embodiment, the angiopoietin receptor is Tie2. Preferably the polypeptide comprises a modified Tie2 ectodomain.

In one embodiment, the polypeptide comprises a variant of human Tie2 comprising 1 to 30 amino acid variations with respect to SEQ ID NO:1 or SEQ ID NO:2 or a fragment thereof.

In another embodiment, the polypeptide comprises a variant of SEQ ID NO:2 or residues 23-210 of SEQ ID NO:1, the variant comprising 1 to 30 amino acid substitutions, deletions or insertions compared to SEQ ID NO:2 or residues 23-210 of SEQ ID NO:1.

In another embodiment, the polypeptide has at least 90% sequence identity to at least 50 amino acid residues of SEQ ID NO:1 or SEQ ID NO:2.

The polypeptide preferably comprises one or more mutations with respect to SEQ ID NO:1 or SEQ ID NO:2 or a fragment thereof selected from: F161G, F161I, ΔR167, ΔH168, V154L, P171A, E169D, V170I and T226S.

In a preferred embodiment, the polypeptide comprises the mutation F161I. In another preferred embodiment, the polypeptide comprises the mutation F161G. In another preferred embodiment, the polypeptide comprises the mutation ΔR167/ΔH168. In a particularly preferred embodiment, the polypeptide comprises the mutations F161I, ΔR167 and ΔH168. In another particularly preferred embodiment, the polypeptide comprises the mutations F161G, ΔR167 and ΔH168.

In one embodiment, the polypeptide has at least 90% sequence identity to at least 50 amino acid residues of SEQ ID NO:3, e.g. the polypeptide may comprise at least 50 amino acid residues of SEQ ID NO:3.

In some embodiments, fragment as described above are at least 50 amino acid residues in length.

In one embodiment, the polypeptide binds to Ang2 and Ang1 with an affinity ratio of at least 10:1. For instance, the polypeptide may bind to Ang2 with a Kd of less than 10 nM, and/or the polypeptide may bind to Ang1 with a Kd of greater than 1 μM.

In a further aspect, the invention provides a nucleic acid encoding a polypeptide as described above.

In one embodiment, the nucleic acid comprises a variant of SEQ ID NO:4 or SEQ ID NO:5 or a portion thereof comprising one or more nucleotide substitutions, deletions or insertions as shown in FIG. 9 or FIG. 10A.

In a further aspect, the invention provides an expression vector comprising a nucleic acid as described above.

In a further aspect, the invention provides a host cell comprising an expression vector as described above.

In a further aspect, the invention provides a pharmaceutical composition comprising a polypeptide or nucleic acid as described above and a pharmaceutically acceptable carrier, diluent or excipient.

In a further aspect, the invention provides a polypeptide, nucleic acid or pharmaceutical composition as described above, for use in the prevention or treatment of an angiopoietin-2-mediated disease or condition.

In a further aspect, the invention provides use of a polypeptide, nucleic acid or pharmaceutical composition as described above, for the preparation of a medicament for preventing or treating an angiopoietin-2-mediated disease or condition.

In a further aspect, the invention provides a method for preventing or treating an angiopoietin-2-mediated disease or condition in a subject in need thereof, comprising administering to the subject a pharmaceutically effective amount of a polypeptide, nucleic acid or pharmaceutical composition as described above.

In one embodiment, the disease or condition is cancer, inflammation, sepsis, angiogenesis, oedema, retinopathy, age-related macular degeneration or hypertension.

Embodiments of the present invention provide a variant form of a Tie2 ectodomain which preferentially binds Ang2 and which can be used to block the damaging effects of this ligand without suppressing the protective effects of Ang1. This was achieved by combining SHM-driven gene diversification with surface display in a B cell line to evolve a form of Tie2 ectodomain with preferential binding to Ang2.

BRIEF DESCRIPTION OF DRAWINGS

FIGS. 9A-9B. Mutations in non expressing DT40 population. Genomic DNA was prepared from non-expressing DT40, selected by FACS following staining with anti-FLAG and Ang1 binding, and used for amplification of DNA encoding Tie2 ectodomain. Thirty randomly selected colonies were sequenced following transformation into *E Coli*. The primary nucleic acid sequence shown (designated herein SEQ ID NO: 4) encodes the human Tie2 ectodomain, i.e. residues 1-442 of SEQ ID NO: 1 (which is designated herein as SEQ ID NO: 2). For mutated nucleotides, the substituted nucleotide shown is above, dash indicates a deletion. Some mutations did not affect expression but these were accompanied by a deletion that ablated expression.

FIG. 10. Mutations in R3 Ang2-specific binding population. Genomic DNA was prepared from the R3 population shown in FIG. 5 and used for amplification of DNA encoding Tie2 ectodomain. Twenty randomly selected sequences were sequenced following transformation into *E Coli*. (A) The primary nucleic acid sequence shown (designated herein SEQ ID NO: 5) comprises residues 401-750 of SEQ ID NO: 4. For mutated nucleotides, the substituted nucleotide is shown above, dash indicates a deletion. The nucleotide changes found in all twenty sequences are underlined. (B) The primary amino acid sequence shown (designated herein SEQ ID NO:6) comprises residues 101-300 of SEQ ID NO:1. Amino acid changes resulting from mutations are shown, changes found in all twenty sequences are underlined.

FIGS. 12A-12C. Amino acid sequence of human Tie 2. The full length amino acid sequence of human Tie2 (SEQ ID NO:1), as described in database accession no. Q02763, is shown.

DETAILED DESCRIPTION

Figure 1C:
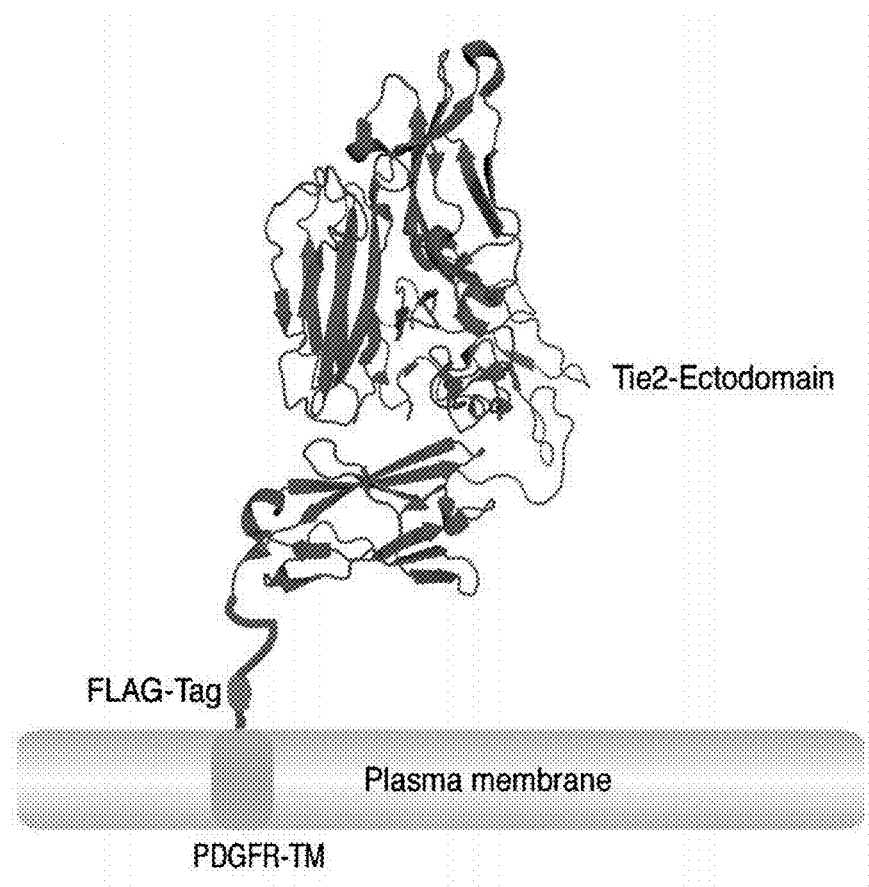
FIG. 1. Directed evolution of receptor ectodomain. (A) Strategy for directed evolution in hypermutating B cells. (B) Alignment of the receptor binding P-domains of human Ang1 (SEQ ID NO: 7) and Ang2 (SEQ ID NO: 8). (C) Schematic representation of the surface expression construct incorporating residues 1-442 of Tie2 and used for directed evolution. (D) Anti-FLAG immunofluorescent staining of DT40 cells transfected with surface expression construct. (E) Flow cytometry of DT40 cells expressing Tie2 ectodomain. Untransfected (left plot) and transfected (right plot) cells were allowed to bind $His_6$-tagged 1 nM Ang1 or Ang2 or no ligand for 30 min before staining with anti-His and fluorescent secondary antibody.

In one aspect the present invention relates to a polypeptide comprising a modified angiopoietin receptor or fragment thereof, wherein the polypeptide binds preferentially to angiopoietin-2 compared to angiopoietin-1.

Angiopoietin Receptors

By "angiopoietin receptor" it is meant an agent which binds selectively or specifically to angiopoietin. Preferably the angiopoietin receptor is Tie2 (Tyrosine kinase with Ig and EGF homology domains-2), which may also be known as: Tyrosine-protein kinase receptor TIE-2; Angiopoietin-1 receptor; Endothelial tyrosine kinase; Tunica interna endothelial cell kinase; Tyrosine-protein kinase receptor TEK; p140 TEK; and CD antigen 202b. Tie2 is classified as a receptor tyrosine kinase in class EC=2.7.10.1 according to the IUBMB Enzyme Nomenclature. The amino acid sequence of human Tie2 may be found under UniProtKB/Swiss-Prot database accession number Q02763, and is shown in SEQ ID NO:1 (FIG. 12).

Modified Angiopoietin Receptors and Fragments Thereof

The polypeptide described herein comprises a modified angiopoietin receptor or fragment thereof. By "modified" it is meant that the polypeptide sequence comprises one or more differences (e.g. amino acid substitutions, deletions or insertions) with respect to a wild type angiopoietin receptor, e.g. compared to human Tie2 (Q02763, as shown in SEQ ID No:1 and FIG. 12). The polypeptide may thus be a variant, mutant or other modified form of an angiopoietin receptor, preferably of human Tie2.

Preferably the polypeptide comprises at least two or at least three amino acid changes with respect to the wild type angiopoietin receptor. In particular embodiments, the polypeptide may comprise 1 to 30, 1 to 20, 1 to 10, 1 to 5, 2 to 30, 2 to 20, 2 to 10 or 2 to 5 amino acid differences compared to a corresponding sequence in the wild type receptor or a fragment thereof, e.g. compared to human Tie2 (SEQ ID NO:1) or a fragment thereof.

Amino acid changes may include substitutions, deletions or insertions. Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native sequence. Immediately adjacent to an amino acid means connected to either the alpha-carboxy or alpha-amino functional group of the amino acid.

Deletional variants are those with one or more amino acid residues in a native sequence removed. For example, deletional variants may have one, two or more amino acid residues deleted in a particular region of the molecule. Deletional mutations are represented herein by the symbol Δ.

By "fragment" it is meant a portion of the full length sequence of an angiopoietin receptor, typically which is capable of folding independently and/or which retains one or more structural or biological properties of the full length sequence. Thus fragments as described herein are capable of preferentially binding to Ang2 compared to Ang1. Preferred fragments are typically 10 to 1000, 20 to 800, 30 to 500, 30 to 800, 30 to 500, 50 to 500, 50 to 300, or 100 to 200 amino acid residues in length.

In some embodiments, the fragment comprises substantially all, or at least a portion of, the extracellular domain (ectodomain) of the angiopoietin receptor. The term "extracellular domain" or "ectodomain" refers to the amino acid sequences in an angiopoietin receptor that are normally exposed on the outer surface of the cell membrane and which are typically involved in binding to Ang2. Extracellular and ligand binding domains in angiopoietin receptors may be determined by methods known in the art, including X-ray studies, mutational analyses, and antibody binding studies. The mutational approaches include the techniques of random saturation mutagenesis coupled with selection of escape mutants, and insertional mutagenesis. Another strategy suitable for identifying ligand-binding domains in receptors is known as alanine (Ala)-scanning mutagenesis. See e.g. Cunningham, et al., Science 244, 1081-1985 (1989). This method involves the identification of regions that contain charged amino acid side chains. The charged residues in each region identified (i.e. Arg, Asp, His, Lys, and Glu) are replaced (one region per mutant molecule) with Ala and the ligand binding of the obtained receptors is tested, to assess the importance of the particular region in ligand binding. A further method for the localization of ligand binding domains is through the use of neutralizing antibodies. Usually a combination of these and similar methods is used for localizing the domains which are extracellular and are involved in binding to Ang2.

In one embodiment, the polypeptide comprises an amino acid sequence which is homologous to at least residues 1-442 or residues 23-210 of human Tie2. Residues 1-442 of human Tie2 are shown in FIG. 3A and are defined herein as SEQ ID NO:2. For instance, the polypeptide may comprise a sequence which is a variant or homologue of residues 1-442 or residues 23-210 of SEQ ID NO:1, e.g. comprising 1 to 30, 1 to 10 or 1 to 5 amino acid substitutions, deletions or additions compared to residues 1-442 or residues 23-210 of SEQ ID NO:1. In further embodiments, the polypeptide may comprise a variant or homologue of at least residues 100-210, 150-210 or 150-170 of SEQ ID NO:1.

Preferably, the modified angiopoietin receptor or fragment thereof shows at least 70%, at least 80%, at least 90%, at least 95%, at least 97%, at least 98% or at least 99% homology or sequence identity to a portion of the wild type angiopoietin receptor, e.g. over at least 30, at least 50, at least 100, at least 200, at least 300 or at least 500 amino acid residues or over the full length of the sequence. The term "homology" can be equated with "sequence identity". For instance, the polypeptide may have any of the above degrees of sequence identity to SEQ ID NO:1, SEQ ID NO:2 or a fragment thereof, e.g. over at least 30, 100 or 300 amino acid residues of SEQ ID NO:1 or SEQ ID NO:2 or to residues 1-442 or residues 23-210 of SEQ ID NO:1.

Sequence identity comparisons can be conducted by eye, or more usually, with the aid of readily available sequence comparison programs. These commercially available computer programs use complex comparison algorithms to align two or more sequences that best reflect the evolutionary events that might have led to the difference(s) between the two or more sequences. Therefore, these algorithms operate with a scoring system rewarding alignment of identical or similar amino acids and penalising the insertion of gaps, gap extensions and alignment of non-similar amino acids. The scoring system of the comparison algorithms include:

i) assignment of a penalty score each time a gap is inserted (gap penalty score), ii) assignment of a penalty score each time an existing gap is extended with an extra position (extension penalty score), iii) assignment of high scores upon alignment of identical amino acids, and iv) assignment of variable scores upon alignment of non-identical amino acids.

Most alignment programs allow the gap penalties to be modified. However, it is preferred to use the default values when using such software for sequence comparisons.

The scores given for alignment of non-identical amino acids are assigned according to a scoring matrix also called a substitution matrix. The scores provided in such substitution matrices are reflecting the fact that the likelihood of one amino acid being substituted with another during evolution varies and depends on the physical/chemical nature of the amino acid to be substituted. For example, the likelihood of a polar amino acid being substituted with another polar amino acid is higher compared to being substituted with a hydrophobic amino acid. Therefore, the scoring matrix will assign the highest score for identical amino acids, lower score for non-identical but similar amino acids and even lower score for non-identical non-similar amino acids. The most frequently used scoring matrices are the PAM matrices (Dayhoff et al. (1978), Jones et al. (1992)), the BLOSUM matrices (Henikoff and Henikoff (1992)) and the Gonnet matrix (Gonnet et al. (1992)).

Suitable computer programs for carrying out such an alignment include, but are not limited to, Vector NTI (Invitrogen Corp.) and the ClustalV, ClustalW and ClustalW2 programs (Higgins D G & Sharp P M (1988), Higgins et al. (1992), Thompson et al. (1994), Larkin et al. (2007). A selection of different alignment tools are available from the ExPASy Proteomics server at www.expasy.org. Another example of software that can perform sequence alignment is BLAST (Basic Local Alignment Search Tool), which is available from the webpage of National Center for Biotechnology Information which can currently be found at http<colon-slash-slash>www.ncbi.nlm.nih.gov/ and which was firstly described in Altschul et al. (1990) J. Mol. Biol. 215; 403-410.

Once the software has produced an alignment, it is possible to calculate % similarity and % sequence identity. The software typically does this as part of the sequence comparison and generates a numerical result.

In one embodiment, it is preferred to use the ClustalW software for performing sequence alignments. Preferably, alignment with ClustalW is performed with the following parameters for pairwise alignment:

| | |
|---|---|
| Substitution matrix: | Gonnet 250 |
| Gap open penalty: | 20 |
| Gap extension penalty: | 0.2 |
| Gap end penalty: | None |

ClustalW2 is for example made available on the internet by the European Bioinformatics Institute at the EMBL-EBI webpage www<dot>ebi.ac.uk under tools—sequence analysis—ClustalW2. Currently, the exact address of the ClustalW2 tool is www<dot>ebi.ac.uk/Tools/clustalw2.

In another embodiment, it is preferred to use the program Align X in Vector NTI (Invitrogen) for performing sequence alignments. In one embodiment, Exp10 has been may be used with default settings:
Gap opening penalty: 10
Gap extension penalty: 0.05

Gap separation penalty range: 8
Score matrix: blosum62mt2

Preferred Mutations

In some embodiments, the polypeptide comprises one or more mutations compared to the wild type Tie2 ectodomain sequence as described below in the Examples. In one embodiment, the polypeptide comprises one or more mutations (e.g. substitutions, deletions or insertions) at residues 150 to 230 of the human Tie2 sequence (SEQ ID NO:1) or a fragment thereof (e.g. SEQ ID NO:2). Preferably the polypeptide comprises one or more mutations within the region 150 to 180, more preferably 160 to 175, most preferably 160 to 170 of SEQ ID NO:1 or 2.

In one embodiment, the polypeptide comprises a mutation at one or more of the following positions in the human Tie2 sequence (SEQ ID NO:1) or a fragment thereof (e.g. SEQ ID NO:2): 154, 161, 167, 168, 169, 170, 171 and 226. Preferably the polypeptide comprises a mutation at one, two or three of positions 161, 167 and 168 of SEQ ID NO:1 or 2.

Preferably the polypeptide comprises one or more of the following mutations with respect to the human Tie2 sequence (SEQ ID NO:1) or a fragment thereof (e.g. SEQ ID NO:2): F161G, F161I, ΔR167, ΔH168, V154L, P171A, E169D, V170I and T226S.

In one embodiment, the polypeptide comprises the mutation F161I. In another embodiment, the polypeptide comprises the mutation ΔR167/ΔH168. In one embodiment, the polypeptide comprises at least the following combination of mutations: F161I, ΔR167 and ΔH168, e.g. with respect to SEQ ID NO:1 or SEQ ID NO:2.

In one embodiment, the polypeptide comprises the mutation F161G. In another embodiment, the polypeptide comprises the mutation ΔR167/ΔH168. In one embodiment, the polypeptide comprises at least the following combination of mutations: F161G, ΔR167 and ΔH168, e.g. with respect to SEQ ID NO:1 or SEQ ID NO:2.

In a particularly preferred embodiment, the polypeptide comprises at least 30, at least 50, as least 100, at least 200, at least 300 amino acid residues, or the full length of SEQ ID NO:3, i.e. the sequence of SEQ ID NO:2 modified by the mutations F161I, ΔR167 and ΔH168 (see FIG. 3A). Variants and homologues of SEQ ID NO:3 are also contemplated, e.g. comprising 1 to 30, 1 to 10 or 1 to 5 amino acid substitutions, deletions or additions compared to SEQ ID NO:3, provided that the mutations F161I, ΔR167 and ΔH168 are present. In further embodiments, the polypeptide may comprise a variant or homologue of at least residues 100-210, 150-210 or 150-170 of SEQ ID NO:3. Sequences showing at least 70%, at least 80%, at least 90%, at least 95%, at least 97%, at least 98% or at least 99% homology or sequence identity to at least 30, at least 50, at least 100, at least 200, at least 300 or at least 500 amino acid residues of, or over the full length of, SEQ ID NO:3 are also described, provided that the mutations F161I, ΔR167 and ΔH168 are retained.

In another embodiment, the polypeptide comprises a variant of SEQ ID NO:3 comprising the mutation I161G (with respect to SEQ ID NO:3), or a variant or homologue thereof as described in the preceding paragraph. The mutation I161G with respect to SEQ ID NO:3 corresponds to the mutation F161G with respect to SEQ ID NO:2. Thus in some embodiments the polypeptide comprises at least 70%, 90% or 95% sequence identity to at least 30, at least 100 or over the full length of SEQ ID NO:3, provided that the mutations F161G, ΔR167 and ΔH168 with respect to SEQ ID NO:2 are present.

Further Mutations

Further modified angiopoietin receptors comprising alternative mutations may be constructed using methods analogous to those described herein, with particular reference to the Examples below. For instance, methods for evolving proteins with specificity for a selected target using in vitro somatic hypermutation in cell lines are described in e.g. WO00/22111, WO02/100998 and WO03/095636.

Preferential Binding to Ang2

The polypeptides of the present invention bind preferentially to Ang2 compared to Ang1. In other words, the polypeptides are typically selective for Ang2 over Ang1, e.g. the polypeptides bind with higher affinity to Ang2 than to Ang1 under the same conditions. Binding affinity may be measured using standard techniques known in the art, e.g. surface plasmon resonance, ELISA and so on (for instance as described below in the Examples), and may be quantified in terms of either association ($K_a$) or dissociation ($K_d$) constants.

In a preferred embodiment, the polypeptide binds to Ang2 and Ang1 with an affinity ratio of at least 2:1 (e.g. $K_a$ (Ang2)/$K_a$ (Ang1)≥2). In further embodiments, the polypeptide may have an affinity ratio for Ang2/Ang1 of at least 5:1, at least 10:1, at least 100:1, at least 1000:1 or at least 10,000:1. For instance, the polypeptide may bind to Ang2 with a $K_d$ of less than 100 μM, preferably less than 1 μM, more preferably less than 100 nM, most preferably less than 10 nM. The polypeptide may bind to Ang1 with a $K_d$ of greater than 10 nM, preferably greater than 100 nM, more preferably greater than 1 μM, most preferably greater than 100 μM. In one embodiment the polypeptide does not bind to Ang1 (e.g. the polypeptide shows negligible or substantially no binding to Ang1 under standard assay conditions).

Nucleic Acids, Expression Vectors and Host Cells

Nucleic acid sequences encoding the above-described polypeptides are also provided herein. Suitable nucleic acid sequences can be prepared using methods known in the art based on the published sequences of angiopoietin receptors such as human Tie2. A nucleic acid sequence encoding residues 1-442 of human Tie2 (i.e. the ectodomain) is shown in FIG. 9 (SEQ ID NO:4). Residues 401 to 750 of SEQ ID NO:4 are shown in FIG. 10A (SEQ ID NO:5).

Variant nucleic acid sequences comprising mutations which encode polypeptides according to the present invention are also shown in FIGS. 9 and 10A. Typically such variant sequences show at least 50%, at least 70%, at least 80%, at least 90%, at least 95%, at least 97% or at least 99% sequence identity to SEQ ID NO:4 or SEQ ID NO:5 or a portion thereof, e.g. over at least 50, 100, 200, 500 or 1000 nucleotide residues or over the full length of either sequence, provided that the sequence comprises at least one of the mutations shown in FIG. 9A or 10. Sequence identity may be determined as described above in relation to polypeptide sequences.

Variant nucleic acid sequences encoding modified angiopoietin receptors are readily prepared by methods known in the art, such as by site directed mutagenesis of the DNA encoding the native receptor. Such sequences can be cloned into suitable vectors for expression of the desired recombinant polypeptide in host cells. The term "recombinant" refers to proteins that are produced by recombinant DNA expression in a host cell. The host cell may be prokaryotic (for example, a bacterial cell such as *E. coli*) or eukaryotic (for example, a yeast or a mammalian cell). For example, a nucleic acid encoding the polypeptide may be placed into an expression vector, which is then transfected into host cells such as simian COS cells or Chinese Hamster ovary (CHO) cells. The recombinant host cells are grown in suitable culture medium, and the desired fragment or amino acid sequence variant expressed in the host cells is recovered from the recombinant cell culture by chromatographic or other purification methods.

Conjugates and Fusion Proteins

In some embodiments the polypeptides described herein may be conjugated to further moieties which augment their biological activity. For example, the polypeptides may be fused with heterologous polypeptides, such as viral sequences, with cellular receptors, with cytokines such as TNF, interferons, or interleukins, with polypeptides having procoagulant activity, with cytotoxins, and with other biologically or immunologically active polypeptides. For instance, in one embodiment it may be desirable to kill cells which express Ang2, and this may be achieved by conjugating a cytotoxin (e.g. diptheria, ricin or *Pseudomonas* toxin, or a chemotherapeutic agent) to the polypeptide described above. Such fusions are readily made either by recombinant cell culture methods (e.g. where the polypeptide is fused to a further polypeptide moiety) or by covalently crosslinking the cytotoxic moiety to an amino acid residue side chain or C-terminal carboxyl of the polypeptide, using methods such as disulfide exchange or linkage through a thioester bond (e.g. using iminothiolate and methyl-4-mercaptobutyrimadate).

Diagnostic Uses

The polypeptides described herein may be used in various methods for detecting Ang2, either in vitro or in vivo. For diagnostic applications, the polypeptides may be labeled with a detectable moiety. The detectable moiety can be any one which is capable of producing, either directly or indirectly, a detectable signal. For example, the detectable moiety may be a radioisotope, such as $^{3}H$, $^{14}C$, $^{32}P$, $^{36}S$, or $^{125}I$, a fluorescent or chemiluminescent compound, such as fluorescein isothiocyanate, rhodamine, or luciferin; radioactive isotopic labels, such as, e.g., $^{126}I$, $^{32}P$, $^{14}C$, or $^{3}H$, or an enzyme, such as alkaline phosphatase, beta-galactosidase or horseradish peroxidase.

Any method known in the art for separately conjugating the polypeptide to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982).

The polypeptides described herein may be employed in any assay format, such as competitive binding assays, direct and indirect sandwich assays, and precipitation assays for detecting Ang2.

Competitive binding assays rely on the ability of a labeled standard (which may be labelled Ang2) to compete with the test sample analyte (e.g. human Ang2) for binding with a limited amount of the polypeptides described herein. The amount of Ang2 in the test sample is inversely proportional to the amount of standard that becomes bound to the polypeptide. To facilitate determining the amount of standard that becomes bound, the polypeptide may be insolubilized before or after the competition, so that the standard and analyte that are bound to the polypeptide may conveniently be separated from the standard and analyte which remain unbound.

Sandwich assays involve the use of two polypeptides, each capable of binding to a different portion of the protein to be detected. In a sandwich assay, the test sample analyte is bound by a first polypeptide which is immobilized on a solid support, and thereafter a second polypeptide binds to the analyte, thus forming an insoluble three part complex. See e.g. David & Greene, U.S. Pat. No. 4,376,110. The second polypeptide may itself be labeled with a detectable moiety (direct sandwich assays) or may be measured using an antibody that is labeled with a detectable moiety (indirect sandwich assay). For example, one type of sandwich assay is an ELISA assay, in which case the detectable moiety is an enzyme.

The polypeptides described herein may also be useful for in vivo imaging, wherein a polypeptide labeled with a detectable moiety is administered to a patient, preferably into the bloodstream, and the presence and location of the labeled polypeptide in the patient is assayed. This imaging technique may be useful, for example, in the staging and treatment of neoplasms. The polypeptide may be labeled with any moiety that is detectable in a mammal, whether by nuclear magnetic resonance, radiology, or other detection means known in the art.

Pharmaceutical Formulations

The polypeptides described herein may be formulated into various compositions for pharmaceutical use. Such dosage forms encompass pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of the polypeptide include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations. The polypeptide will typically be formulated in such vehicles at a concentration of about 0.1 mg/ml to 100 mg/mi.

Suitable examples of sustained release preparations include semipermeable matrices of solid hydrophobic polymers containing the polypeptide, which matrices are in the form of shaped articles, e.g. films, or microcapsules. Examples of sustained-release matrices include polyesters, hydrogels (for example, poly(2-hydroxyethyl-methacrylate) as described by Langer et al., J. Biomed. Mater. Res. 15:167 (1981) and Langer, Chem. Tech., 12: 98-105 (1982), or poly(vinylalcohol), polylactides (U.S. Pat. No. 3,773,919), copolymers of L-glutamic acid and gamma ethyl-L-glutamate (Sidman et al., Biopolymers, 22:547 (1983), non-degradable ethylene-vinyl acetate (Langer et al., supra), degradable lactic acid-glycolic acid copolymers such as the Lupron Depot™ (injectable micropheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., resulting in a loss of biological activity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release polypeptide compositions also include liposomally entrapped forms. Liposomes containing the polypeptides may be prepared by methods known in the art, such as described in Epstein, et al., Proc. Natl. Acad. Sci. USA, 82:3688 (1985); Hwang, et al., Proc. Natl. Acad. Sci. USA, 77:4030 (1980); U.S. Pat. No. 4,485,045; U.S. Pat. No. 4,544,545. Ordinarily the liposomes are the small (about 200-800 Angstroms) unilamelar type in which the lipid content is greater than about 30 mol. % cholesterol, the selected proportion being adjusted for the optimal HRG therapy. Liposomes with enhanced circulation time are disclosed in U.S. Pat. No. 5,013,556.

Treatment of Angiopoietin-2 Related Diseases

For therapeutic applications, the polypeptides of the invention are administered to a mammal, preferably a human, in a pharmaceutically acceptable dosage form, including those that may be administered to a human intravenously as a bolus or by continuous infusion over a period of time, by intramuscular, intraperitoneal, intra-cerebrospinal, subcutaneous, intra-articular, intrasynovial, intrathecal, oral, topical, or inhalation routes. The polypeptides also are suitably administered by intratumoral, peritumoral, intralesional, or perilesional routes, to exert local as well as systemic therapeutic effects. The intraperitoneal route may be particularly useful, for example, in the treatment of ovarian tumors.

For the prevention or treatment of disease, the appropriate dosage of polypeptide will depend on the type of disease to be treated, the severity and course of the disease, whether the polypeptides are administered for preventive or therapeutic purposes, previous therapy, the patient's clinical history and response to the polypeptide, and the discretion of the attending physician. The polypeptide is suitably administered to the patient at one time or over a series of treatments.

The polypeptides described herein are useful in the treatment of various angiopoietin-2-related disorders, including neoplastic and non-neoplastic diseases and disorders. The role of Ang2 in various diseases has been confirmed in numerous studies. For example, see the following publications with respect to cancer (Oliner et al. 2004 Cancer Cell 6, 507-16; Mazzieri et al. 2011 Cancer Cell 19, 512-26; Thurston & Daly 2012, CSHLP Perspectives in Medicine); systemic inflammatory states/sepsis (Thurston & Daly 2012, CSHLP Perspectives in Medicine); airway inflammation (Tabruyn et al 2010 Am J Pathol 177, 3233-3243); ocular neovascularisation: diabetic retinopathy, oxygen-induced retinopathy in neonates, and age-related macular degeneration (Rennel et al. 2011 Microcirculation 18, 598-607); arteriovenous malformations (Hashimoto et al. 2001 Circ Res 89, 111-113); pulmonary hypertension (Dewachter et al 2006 Am J Respir Crit Care Med 174, 1025-1033).

Neoplasms and related conditions that are amenable to treatment include breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), and Meigs' syndrome.

Non-neoplastic conditions that are amenable to treatment include inflammation, including chronic inflammation and lung inflammation, sepsis, angiogenesis, oedema, diabetic and other retinopathies, age-related macular degeneration, hypertension rheumatoid arthritis, psoriasis, atherosclerosis, retrolental fibroplasia, neovascular glaucoma, thyroid hyperplasias (including Grave's disease), corneal and other tissue transplantation, nephrotic syndrome, preeclampsia, ascites, pericardial effusion (such as that associated with pericarditis), and pleural effusion.

Depending on the type and severity of the disease, about 1 µg/kg to 15 mg/kg of polypeptide is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic tumor imaging.

According to another embodiment of the invention, the effectiveness of the polypeptide in preventing or treating disease may be improved by administering the polypeptide serially or in combination with another agent that is effective for those purposes, such as tumor necrosis factor (TNF), an antibody capable of inhibiting or neutralizing the angiogenic activity of vascular endothelial growth factor (VEGF), acidic or basic fibroblast growth factor (FGF) or hepatocyte growth factor (HGF), an antibody capable of inhibiting or neutralizing the coagulant activities of tissue factor, protein C, or protein S (see Esmon, et al., PCT Patent Publication No. WO 91/01753, published 21 Feb. 1991), or one or more conventional therapeutic agents such as, for example, alkylating agents, folic acid antagonists, anti-metabolites of nucleic acid metabolism, antibiotics, pyrimidine analogs, 5-fluorouracil, purine nucleosides, amines, amino acids, triazol nucleosides, or corticosteroids. Such other agents may be present in the composition being administered or may be administered separately. Also, the polypeptide is suitably administered serially or in combination with radiological treatments, whether involving irradiation or administration of radioactive substances.

In one embodiment, vascularization of tumors is attacked in combination therapy. One or more polypeptides described herein are administered to tumor-bearing patients at therapeutically effective doses as determined for example by observing necrosis of the tumor or its metastatic foci, if any. This therapy is continued until such time as no further beneficial effect is observed or clinical examination shows no trace of the tumor or any metastatic foci. Then TNF is administered, alone or in combination with an auxiliary agent such as alpha-, beta-, or gamma-interferon, a VEGF antagonist, anti-HER2 antibody, heregulin, anti-heregulin antibody, D-factor, interleukin-1 (IL-1), interleukin-2 (IL-2), granulocyte-macrophage colony stimulating factor (GM-CSF), or agents that promote microvascular coagulation in tumors, such as anti-protein C antibody, anti-protein S antibody, or C4b binding protein (see Esmon, et al., PCT Patent Publication No. WO 91/01753, published 21 Feb. 1991), or heat or radiation.

Since the auxiliary agents will vary in their effectiveness it is desirable to compare their impact on the tumor by matrix screening in conventional fashion. The administration of the polypeptide and auxiliary agent may be repeated until the desired clinical effect is achieved. In instances where solid tumors are found in the limbs or in other locations susceptible to isolation from the general circulation, the therapeutic agents described herein are administered to the isolated tumor or organ. In other embodiments, a FGF or platelet-derived growth factor (PDGF) antagonist, such as an anti-FGF or an anti-PDGF neutralizing antibody, is administered to the patient in conjunction with the polypeptide.

Other Uses

The polypeptides described herein are also useful as affinity purification agents for Ang2. In this process, the polypeptides are immobilized on a suitable support, such a Sephadex resin or filter paper, using methods well known in the art. The immobilized antibody then is contacted with a sample containing the Ang2 to be purified, and thereafter the support is washed with a suitable solvent that will remove substantially all the material in the sample except the Ang2, which is bound to the immobilized polypeptide. Finally, the support is washed with another suitable solvent, such as glycine buffer, pH 5.0, that will release the Ang2 from the polypeptide.

The invention will now be further illustrated with reference to the following non-limiting examples.

Example 1

Materials and Methods

Materials cDNA encoding human Tie2 ectodomain (1-442), and platelet-derived growth factor receptor 13 (residues 514-562 which includes the transmembrane sequence) and with an amino terminal five alanine linker followed by the FLAG epitope, were generated by polymerase chain reaction. These amplification products were ligated into pcDNA3.1 and then transferred to the vector pHypermut2 (23). All constructs were verified by sequencing. Ang1, Ang2, biotinylated Ang2 and mouse Anti-Ang1 were obtained from R & D Systems. Anti-FLAG conjugated to FITC and streptavidin conjugated to phyoerythrin or phycoerythrin/Cy5 were from Sigma and anti-$His_6$ conjugated to allophycocyanin (APC) from AbCam. Goat anti-mouse conjugated to Percp/Cy5.5 was from Biolegend.

Directed Evolution

The DT40 chicken B cell line $AID^RCL4$ (23) was grown in RPMI-1640 with 7% foetal bovine serum and 3% chicken serum at 37° C. and 5% CO2. Transfections were performed by electroporation in 0.4 cm cuvettes using a Gene Pulser (BioRad) at 250V and 950 μF and stable transfectants selected with puromycin. Transfected clones in which the Tie2 construct had integrated into the rearranged Ig locus were identified by PCR as described previously (23). Expression was confirmed by immunoblotting for the epitope tag, and Tie2 ectodomain and surface expression confirmed by immunostaining of non-permeabilized cells.

For ligand binding and fluorescence activated cell sorting DT40 cells were washed in phosphate buffered saline containing 10% foetal bovine serum and incubated with the appropriate ligands for 30 min at room temperature before washing and staining with anti-Ang1, anti-FLAG, anti-$His_6$ or fluorescently-labelled streptavidin (for biotinylated Ang2 detection) and fluorescently-labelled secondary antibodies, as appropriate, at 4° C. Routinely between 50-100 million cells were sorted by FACS and selected cells recovered directly into culture medium for further growth. Cells were grown and sorted repeatedly as described in the Results and Discussion.

In order to sequence the Tie2 surface expression construct exogenously expressed in the DT40 cells genomic DNA was prepared from DT40 cells. The Tie2 ectodomain insert amplified by PCR, cloned into a bacterial sequencing plasmid and transformed into E. coli. Colonies were picked at random and plasmids sequenced.

Expression of Soluble Ectodomains

For expression in Hek293 cells, cDNA encoding wild-type Tie2 ectodomain (1-442) was subcloned into pcDNA 3.1 upstream of a human Fc tag and C-terminal $His_6$ sequence (kindly supplied by Dr Richard Kammerer). Site directed mutagenesis was used to modify this wild-type sequence to correspond to the evolved mutants. Site directed mutagenesis was performed essentially using the Quick-Change protocol (Agilent Technologies) and confirmed by sequencing.

Soluble ectodomain-Fc fusion proteins were obtained by transfection of HEK293 cells in suspension using polyethylenimine (28) and cells grown for 3-4 days to allow the fusion proteins to accumulate in the medium. Debris was removed from medium by centrifugation and fusion protein purified by Ni-NTA chromatography (Qiagen) followed by buffer exchange into tris buffered saline containing 10% glycerol. Protein concentrations were determined by Bradford assay. Proteins were stored at 4° C.

Binding Assays

Surface plasmon resonance was performed using a Forte-Bio Octet instrument (Pall Life Sciences). Fusion proteins were immobilised at 5 μg/ml on sensors and kinetic binding assays perfoinied as detailed by the manufacturer.

ELISA assays were performed in 96 well plates in which 5 μg/ml Ang1 or Ang2 was immobilized. Following blocking with TBS containing 1 mg/ml BSA and 0.1% Triton-X100 different concentrations of fusion protein were allowed to bind for 1 hour and after washing bound fusion proteins detected with anti-Tie2 ectodomain antibodies followed by peroxidase-conjugated secondary antibody and colourimetric quantification.

Cellular Assays

The endothelial cell line EA.hy926 was cultured in DMEM containing 10% foetal bovine serum at 37° C. and 5% CO2. Cells were quiesced by incubation in serum-free medium before activation with Ang1, Ang2 or both in the absence or presence of 25 μg/ml wild-type or evolved ectodomain-Fc for 30 mins. After washing, cells were lysed and equal amounts of cellular proteins were resolved by SDS/PAGE before detection of S473-phospho-Akt and total Akt by immunoblotting.

Migration assays were performed in Transwell tissue culture wells containing 8 μm pore size inserts (Becton-Dickinson, UK). Serum-free medium containing 250 μg/ml BSA together with Ang1 or Ang2 in the absence or presence of soluble ectodomain-Fc fusion protein was placed in the lower chamber of the wells. $10^5$ endothelial cells in serum-free medium containing 250 μg/ml BSA were placed in the upper chambers and cells were allowed to migrate for 4 h at 37° C. Cells on the upper surface were gently removed with a cotton bud and the membrane fixed in 4% formaldehyde. Membranes were washed in PBS and nuclei stained with DAPI (0.1 μg/ml). Membranes were mounted in glycerol and the numbers of cells migrating through the membrane were counted magnification in 5 random fields on the underside of each insert membrane.

Results and Discussion

Figure 1D:
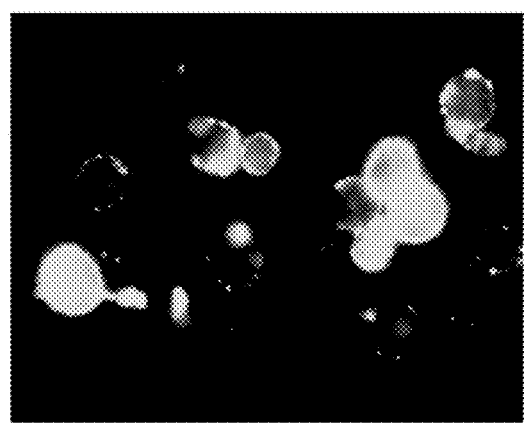
Figure 1E:
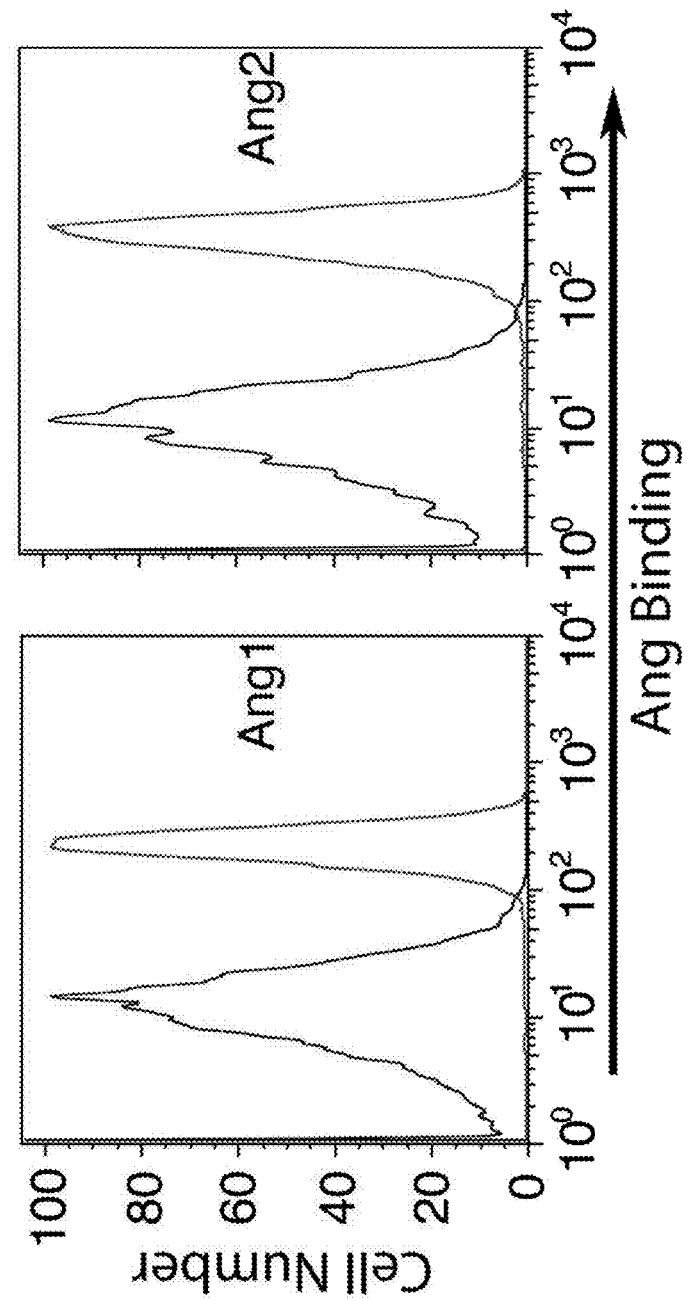
Figure 6:
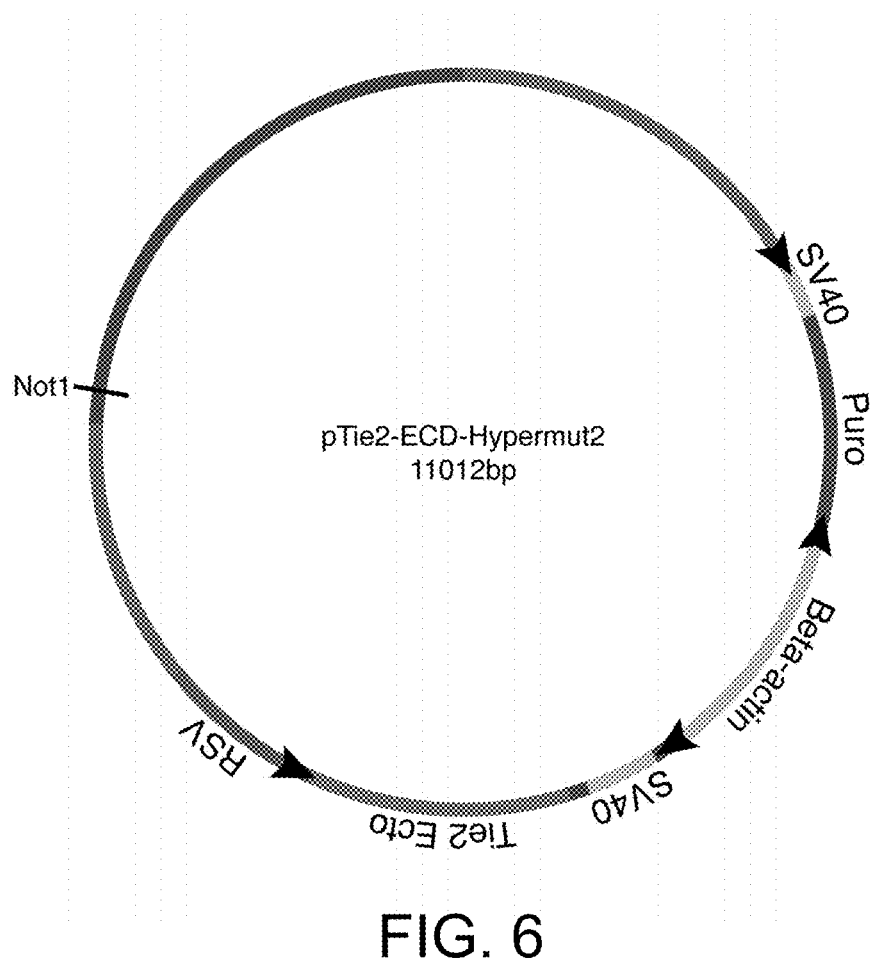
FIG. 6. Plasmid map of the Tie2-Hypermut2 surface expression plasmid. RSV promoter and downstream Tie2 surface display sequence is shown along with Ig homology regions, SV40 polyA sequences, and beta-actin promoter. The approximate position of the Not1 restriction site used for plasmid linearization is also shown.
Figure 7A:
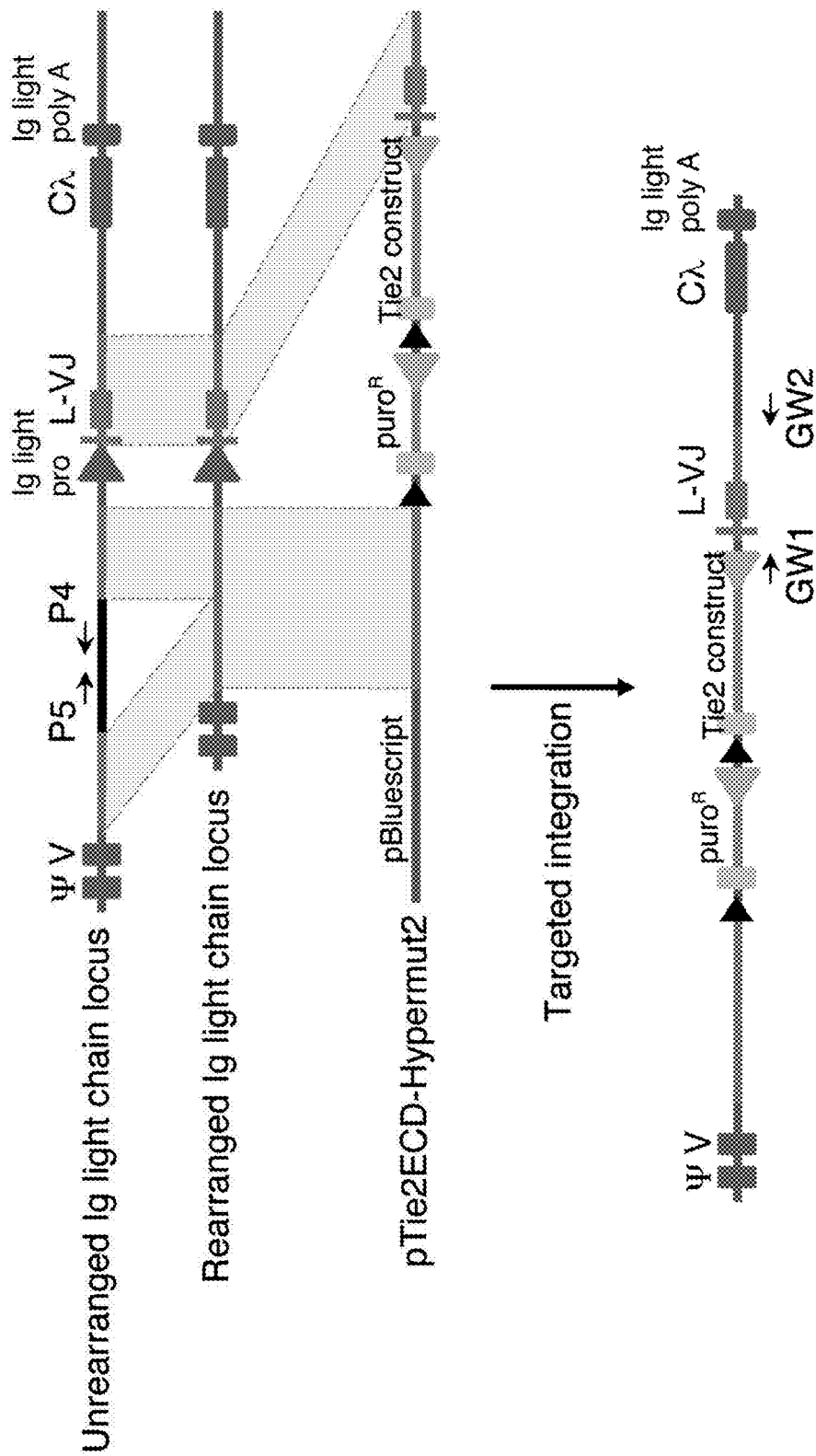
FIG. 7. Targeted integration of Tie2-Hypermut2 into DT40 Ig locus. (A) Schematic representation of unrearranged and rearranged Ig locus and Tie2-Hypermut2 with regions of homology (pink) and integrated construct. The positions of primers P4 and P5 are indicated. PCR of DT40 genomic DNA from transfectants with P4/P5 amplify a 493 bp segment, confirmed in (B) for three representative clones, if integration has not occurred in the unrearranged locus. PCR amplification of genomic DNA from transfected DT40 with primers GW1/GW2 amplify a 1189 bp segment when Tie2-Hypermut2 inegrates into rearranged locus, shown for three clones in (C). Control amplifications (Cont) without DNA and amplifications from untransfected DT40 genomic DNA (Unt) are also shown, ns indicates a non-specific amplification product.
Figure 7B:
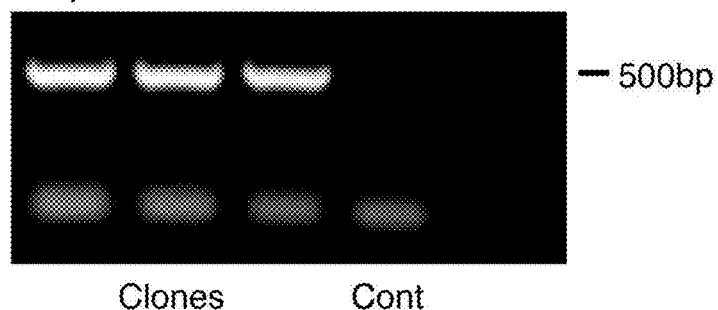
Figure 7C:
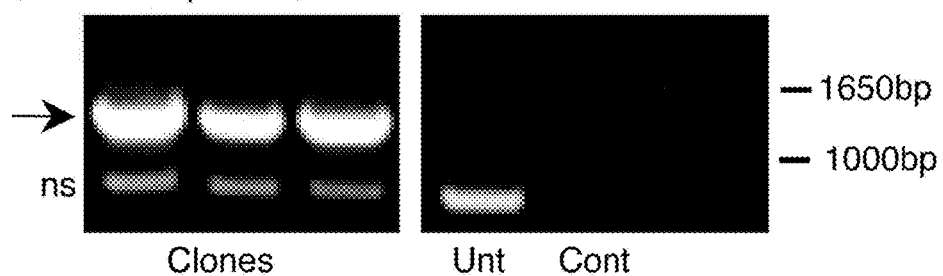
Figure 8:
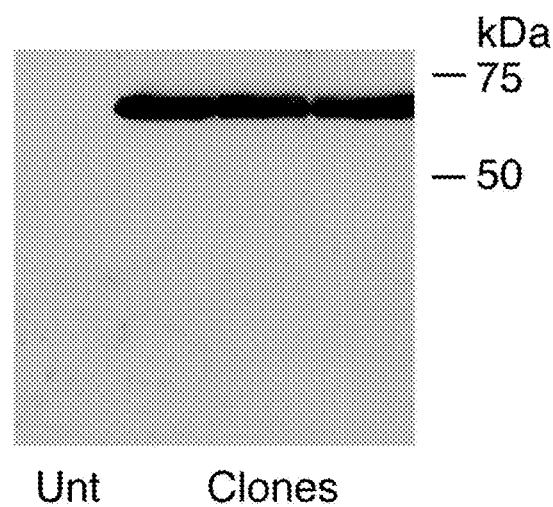
FIG. 8. Anti-FLAG immunoblot of DT40 cells. Cell lysates were prepared from untransfected (Unt) DT40 and three transfected clones and immunoblotted for the FLAG epitope tag.

Combining cell surface display with the ability of certain B cell lines to diversify genes targeted to immunoglobulin loci could provide a powerful strategy for directed evolution of protein binding and other functions (FIG. 1A). Therefore we used this approach to seek to evolve a Tie2 ectodomain that preferentially binds Ang2 better than the protective ligand Ang1, with which it shares more than 70% amino acid sequence identity in its receptor binding domain (FIG. 1B). To do this a cDNA sequence encoding residues 1-442 of the Tie2 ectodomain together with a linker sequence, epitope tag and PDGF receptor transmembrane domain was constructed for surface expression of the ectodomain in B-cells (FIG. 1C). The epitope tag was incorporated to allow quantification of surface expression levels. Previous work has shown that angiopoietin binding only requires residues 23-210 of Tie2 (24). However, it is known that in other proteins mutations at sites remote from the interaction domain can often affect binding ability (25) and for this reason we included additional portions of Tie2 ectodomain beyond residue 210 in our directed evolution strategy. The cDNA construct was cloned into a vector, pHypermut2 (23), for targeted integration into the Ig locus of the chicken cell line DT40 (FIG. 6). Chicken B cells normally diversify their Ig loci by a combination of gene conversion, using an array of upstream IgV pseudogene segments, and by untemplated somatic hypermutation. We used a variant of DT40 in which the IgV pseudogene donors have been deleted and that therefore diversifies only by hypermutation (23). Stably transfected clones were selected for expression of the construct from the rearranged IgV locus by immunoblotting and by PCR (FIG. 7, 8). Surface expression was verified by ant-FLAG immunofluorescence (FIG. 1D). We also confirmed that the ectodomain was competent to bind Ang1 and Ang2 by flow cytometry (FIG. 1E). Apparent binding affinities for Ang1 and Ang2 on the cell surface were derived by incubating with different concentrations of Ang1 or Ang2 and flow cytometry (data not shown), revealing an apparent $K_d$ for Ang1 of 0.70+/−0.36 nM (n=5) and for Ang2 of 2.00+/−0.30 nM (n=3).

Figure 2A:
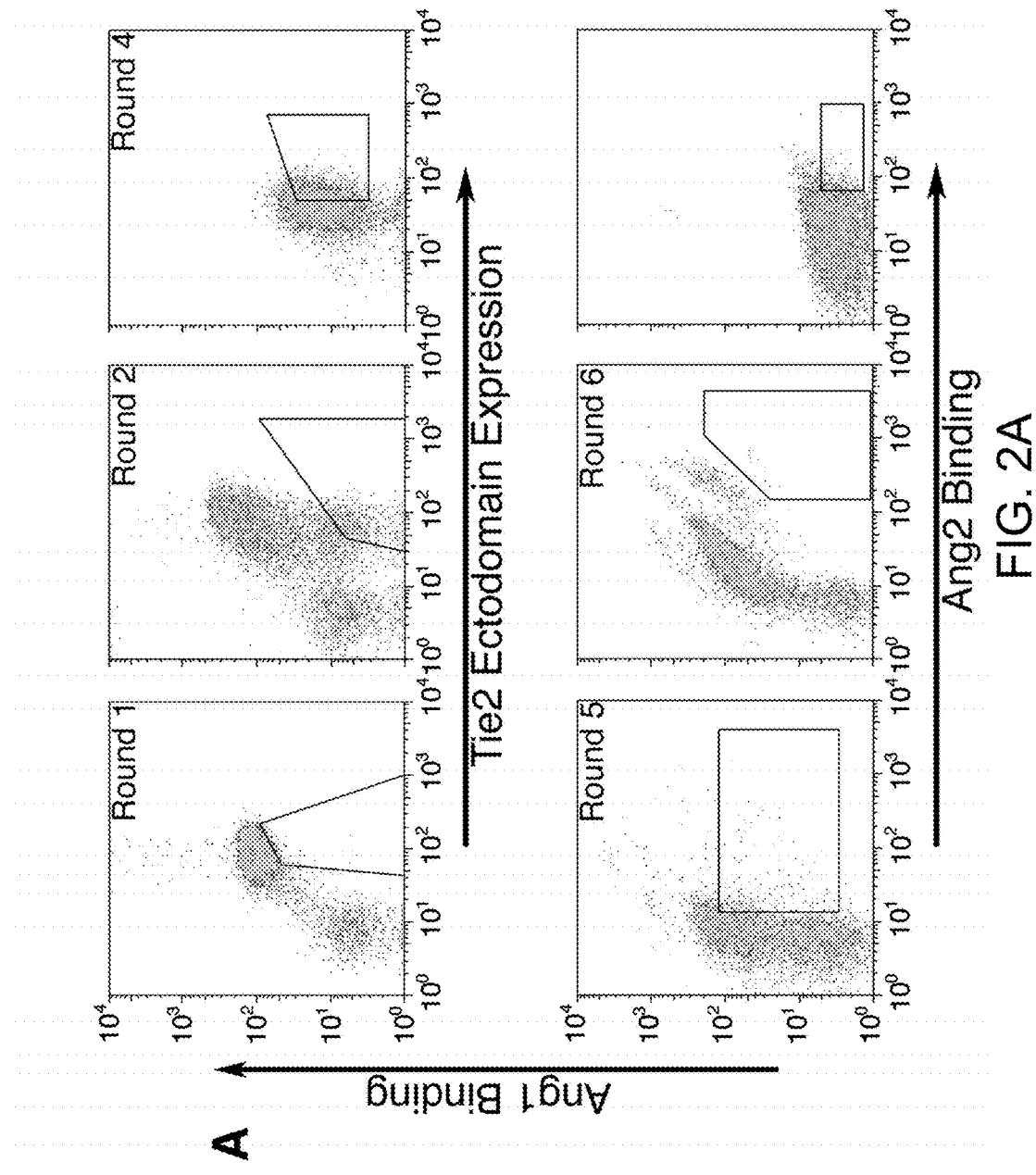
FIG. 2. Evolution of ligand-specific Tie2 ectodomain. (A) FACS plots of DT40 cells following incubation with 1 nM Ang1 and staining with anti-Ang1 and fluorescent secondary antibody together with fluorescent anti-FLAG (Expression). Polygons indicate the gates used to select the cells on sorts 1 (upper plot, left), 2 (upper plot, center) and 4 (upper plot, right) sorts. Cells from sort 4 were then incubated with 1 nM Ang1 and 1 nM biotinylated Ang2 and binding detected with anti-Ang1/fluorescent secondary antibody and fluorescently labelled streptavidin. Cells were selected for highest Ang2 binding. Polygons indicate gates used to select cells on sorts 5 (lower plot, left) and 6 (lower plot, center) sorts. After 8 sorts (lower plot, right) cells were selected for sequencing as indicated by the polygon. (B) Comparison of DT40 cells expressing wild-type receptor with the evolved (R3) population of cells for binding of 1 nM Ang1 and Ang2. Grey plots show fluorescence following staining in the absence of ligand for each population of cells.

In order to evolve Tie2 to preferentially bind Ang2 we used a two-stage strategy, first aiming to decrease the ability of the ectodomain to bind Ang1 and then to test, and if necessary increase, Ang2 binding whilst maintaining low Ang1 binding. For the first stage cells were incubated with Ang1, binding of which was detected by anti-Ang1 and phycoerythrin/Cy5-conjugated secondary antibody, while expression of Tie2 ectodomain construct was monitored with FITC-conjugated anti-FLAG (FIG. 2A). Two subpopulations of cells were observed, one negative for expression of the ectodomain and binding of Ang1, and the other positive for both (FIG. 2A). Sequencing of the Tie2 ectodomain construct from the double negative population confirmed the cells did retain the construct, but that it contained mutations or deletions that would inactivate expression (FIG. 9). Cells positive for expression and with the lowest Ang1 binding were selected by FACS and expanded (FIG. 2A). After four iterations of selection and expansion a population of cells with decreased Ang1 binding compared with parental cells was obtained. We then changed the selection strategy to ensure robust Ang2 binding. We incubated the round 4 cells with Ang1 together and biotinylated Ang2 and monitored binding of the two ligands with fluorescent secondary reagents (FIG. 2A, lower plots). Cells with highest Ang2 binding and low Ang1 binding were selected by FACS. After four rounds of this selection and expansion regime a population of cells with apparent preferential binding to Ang2 was evolved, which we designated R3.

Figure 2B:
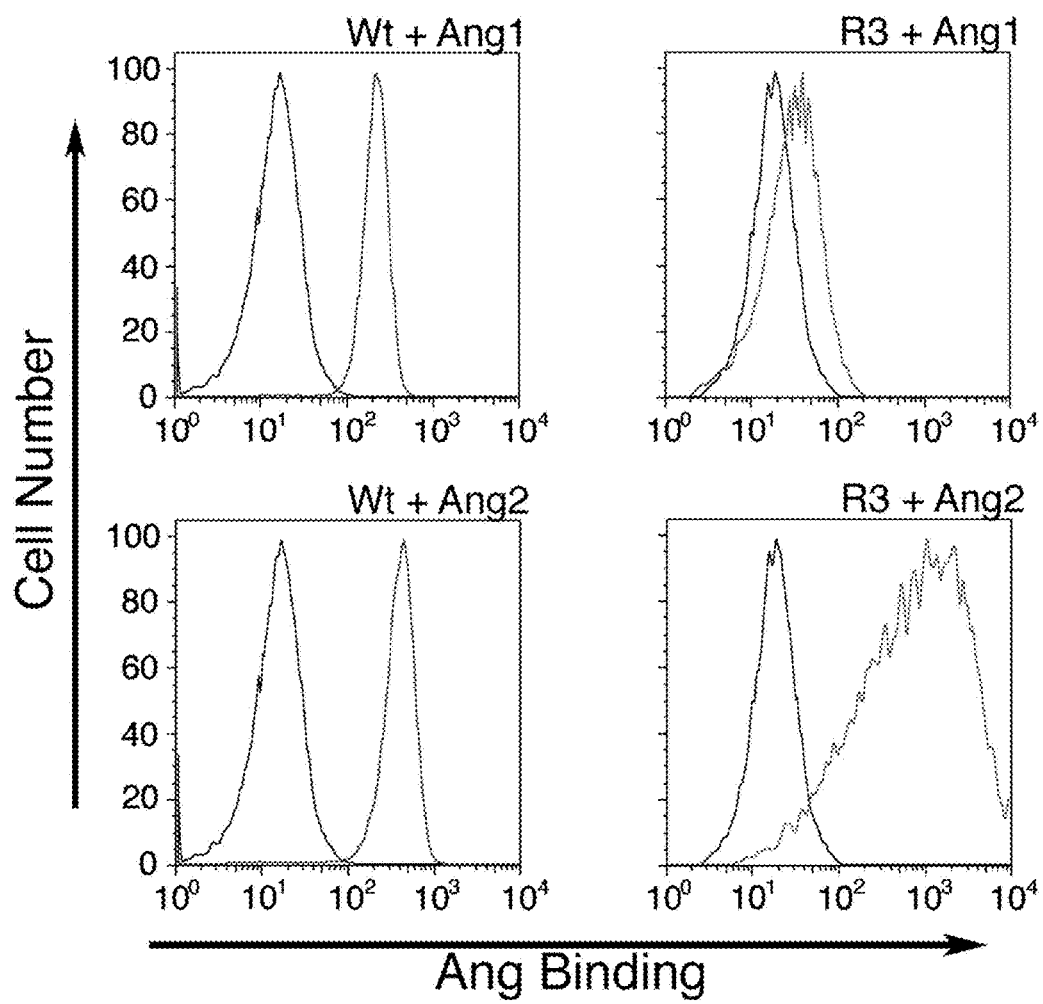

Direct comparison of parental and R3 cells for their ability to bind Ang1 and Ang2 was performed for each of the ligands (FIG. 2B). Cells in the R3 population appeared only able to bind Ang2 and had negligible Ang1 binding whereas parental cells expressing wild-type Tie2 were able to bind both ligands.

Figure 3B:
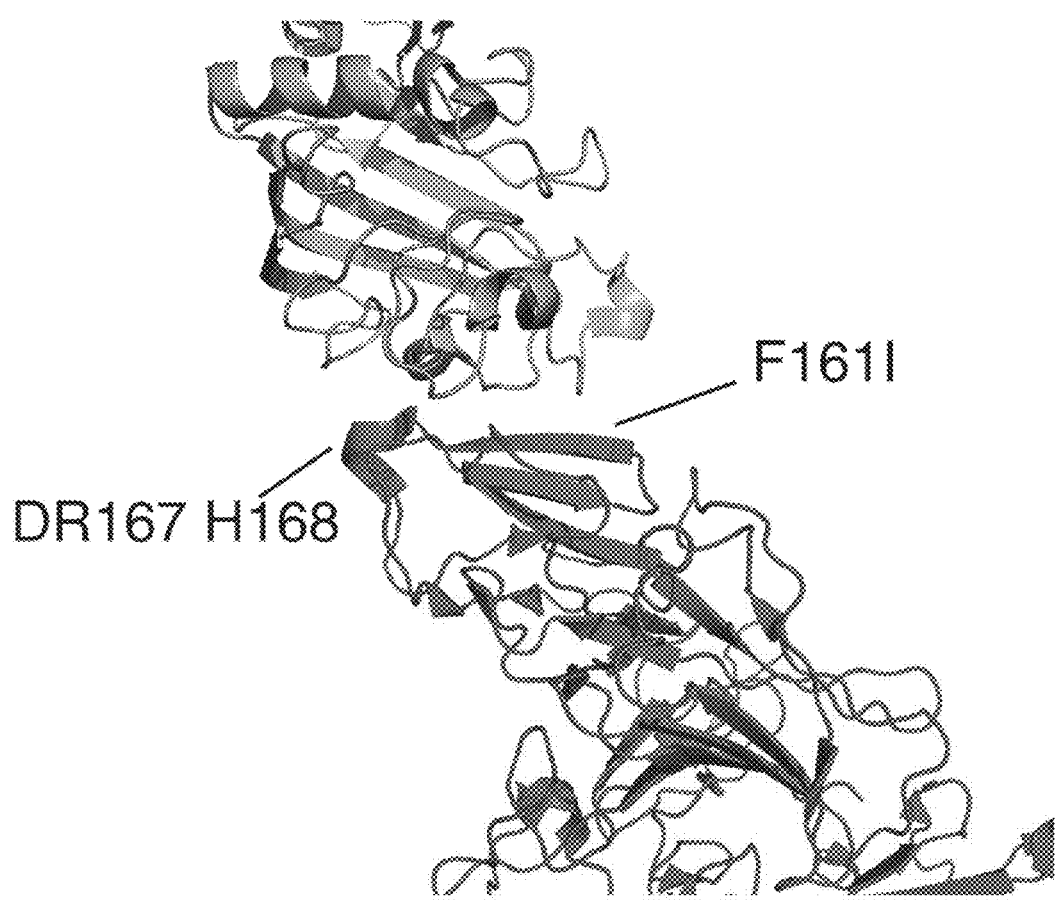
FIG. 3. Three amino acid changes switch the binding specificity of Tie2. (A) The primary sequence shown is residues 1 to 442 of human Tie2, defined herein as SEQ ID NO: 2. Twenty random sequences from R3 cells were determined and all demonstrated F161I substitution and R167, H168 deletion. The sequence shown in this Figure comprising the F161I substitution and R167/H168 deletion is defined herein as SEQ ID NO: 3. (B) The F161I substitution is positioned on a beta sheet and the deletion on a turn at the receptor:ligand interface. Top=Ang2; Bottom=Tie2. Modelled on PDB accession 2GY7 (26).

We next obtained sequences encoding the ectodomain that was expressed on the cells with preferential Ang2 binding (FIG. 2A). Ten sequences were determined and all had a common set of changes, specifically F161 was replaced by I and there was a tandem deletion of R167 and H168 (FIG. 3A). The F/I substitution was the result of a single nucleotide change in the F165 codon from TTC to ATC. The RH double deletion resulted from loss of the final C of codon P166 together with the CGG encoding R167 and the first two nucleotides, CA, of codon H168. This created a new codon for P166, CCT, and removal of R167/H168 (FIG. 10). In addition to these changes a number of other mutations were found in the R3 population, specifically V154L, P171A, E169D, V170I and T226S (FIG. 10), however none of these were present in all sequences. Interestingly, examination of the published structure of Tie2 ectodomain revealed that both the F161I substitution and double R167I168 deletion occur at the binding interface of the receptor for angiopoietins (FIG. 3B).

Figure 4A:
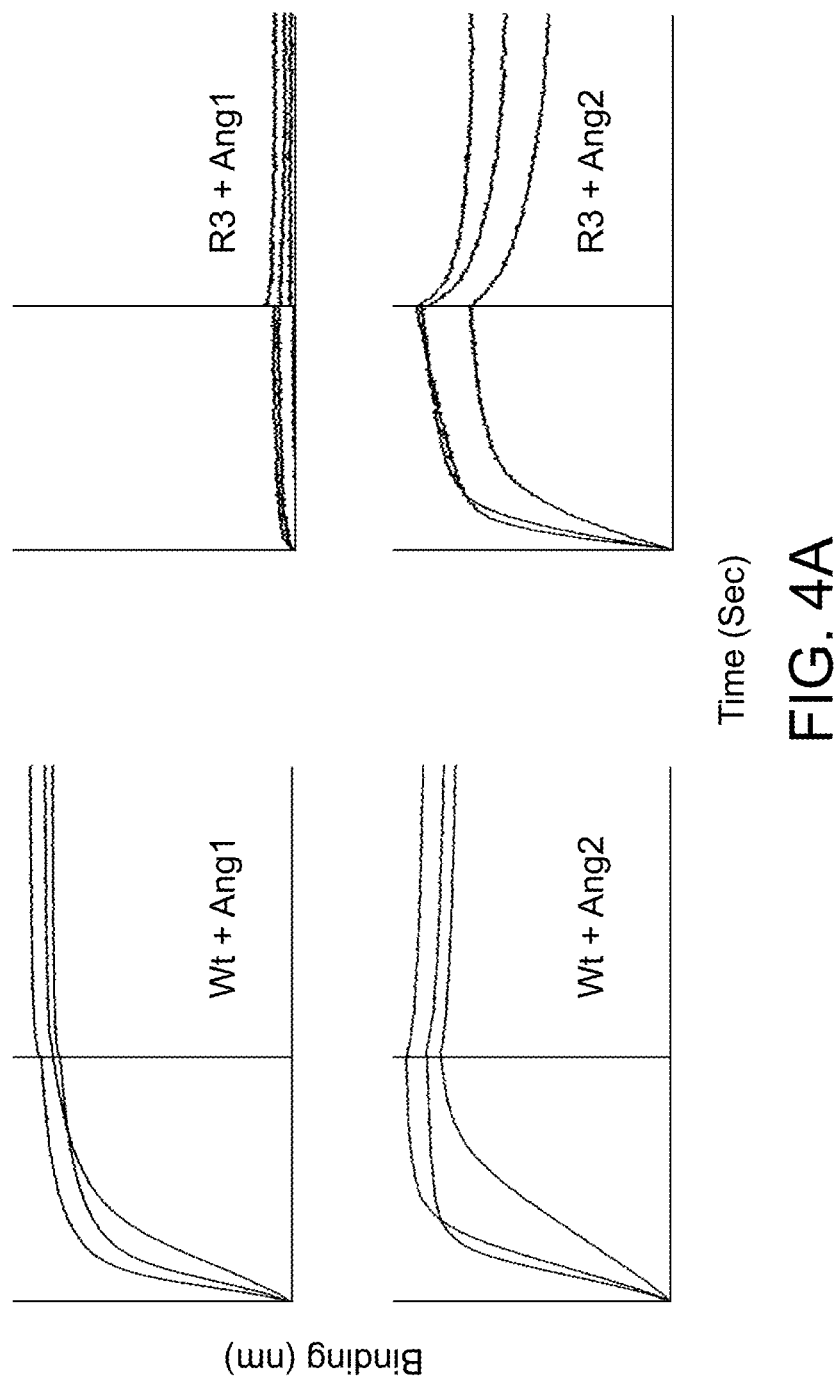
FIG. 4. Evolved ectodomain binds specifically to Ang2. (A) Secreted wild-type and evolved ectodomains were purified following expression in HEK293 cells and immobilized on SPR sensors. Analysis of Ang1 and Ang2 binding to wild-type or evolved ectodomains is shown. (B) Secreted wild-type ectodomain and ectodomains with either F161I substitution or the double R167, H168 deletion were expressed, purified and analysed for binding to immobilized Ang1 or Ang2 by ELISA. Data are shown as means and standard deviations from a single experiment with triplicate determinations performed at least three times.
Figure 4B:
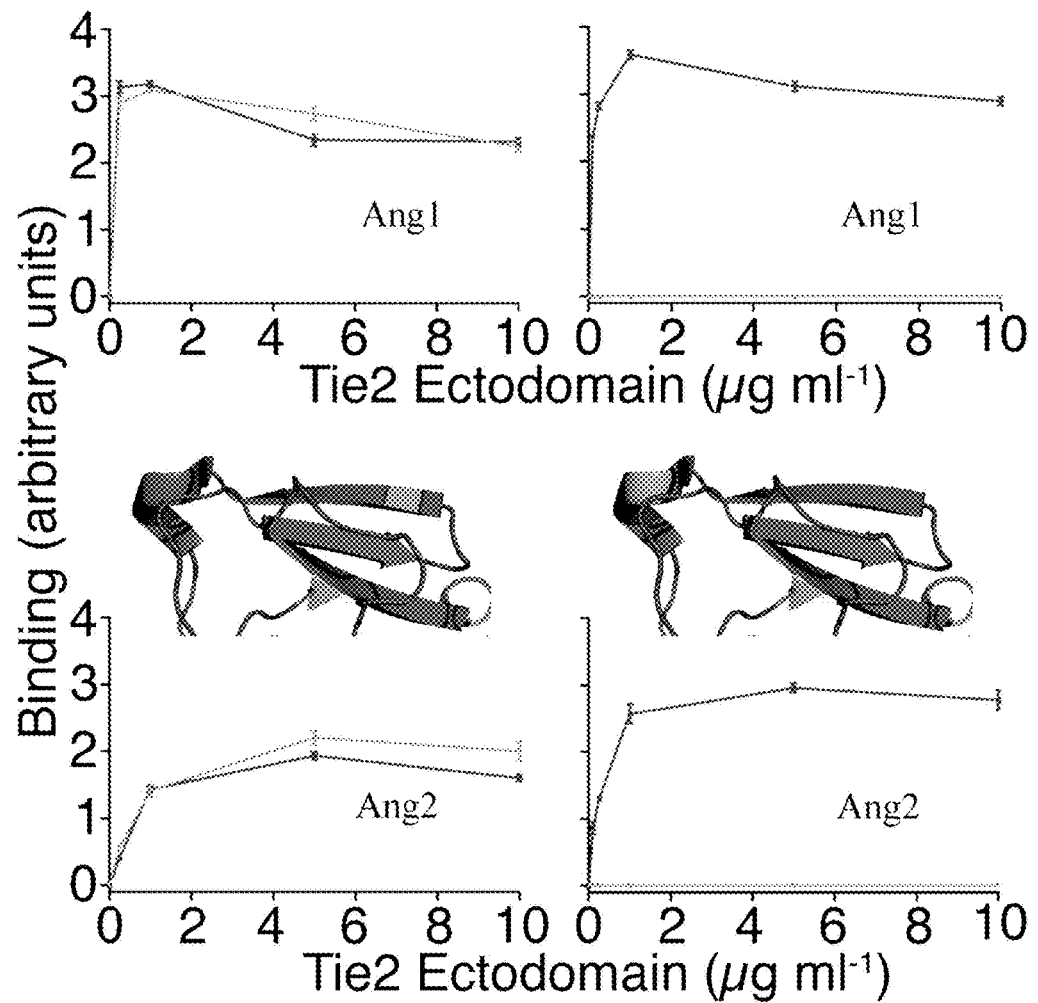
Figures 5A, 5B:
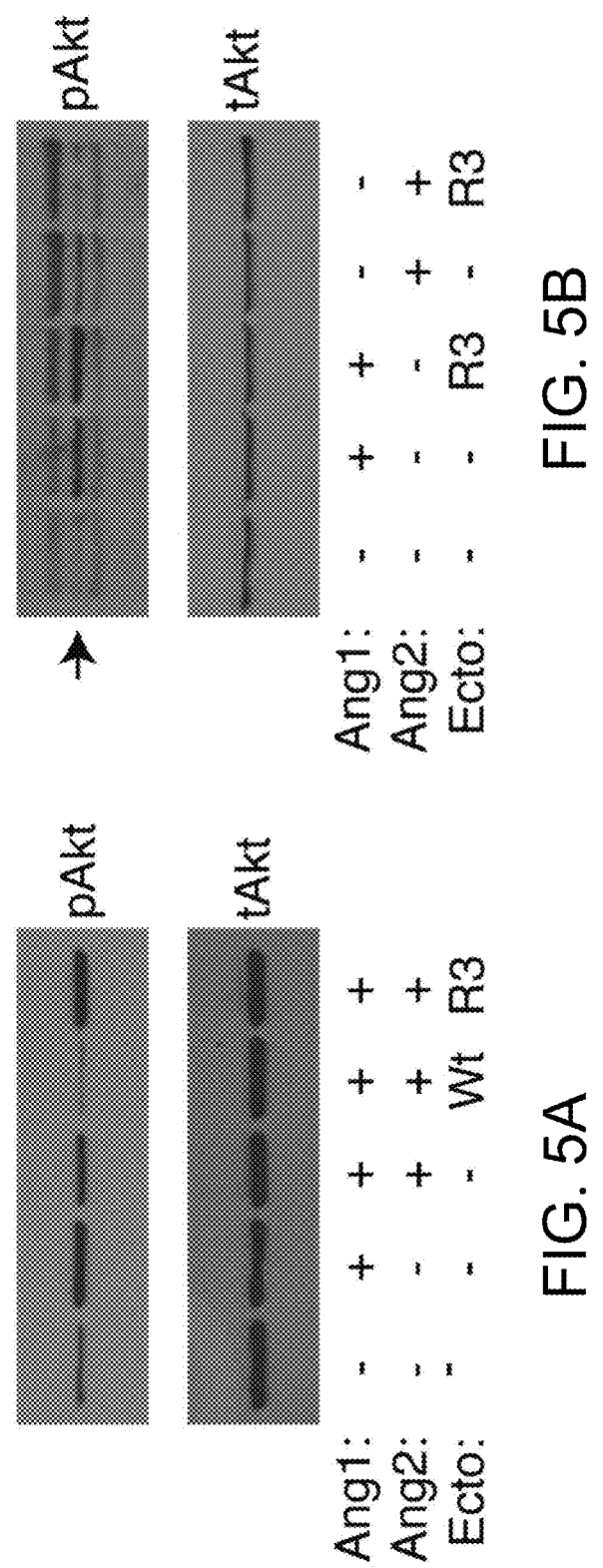
FIG. 5. Evolved ectodomain blocks the effects of Ang2 on endothelial cells. (A) The antagonistic effects of Ang2 on Ang1-activation of Akt phosphorylation were tested in the endothelial cell line EA.hy926. Cells were activated with 50 ng/ml Ang1 in the absence and presence of 200 ng/ml Ang2 and 25 µg/ml wild-type (Wt) or R3 ectodomain for 30 min before cell lysis, gel electrophoresis and immunoblotting with antibodies recognizing Akt phosphorylated on S473 (pAkt) or total AKT (tAkt) as indicated. (B) The agonist activity of 1 µg/ml Ang2 on activation of Akt phosphorylation was tested in the absence and presence of 25 µg/ml R3, for comparison the effects on 50 ng/ml Ang1 are also shown. In order to see the low level of pAkt induced by Ang2 blots were overexposed resulting in the appearance of additional non-specific bands, pAkt is indicated with an arrow. (C) Migration of endothelial cells in response to high concentrations of Ang2 (1 µg/ml) was inhibited by R3 ectodomain whereas this mutant ectodomain did not affect migration in response to Ang1 (50 ng/ml). Data are shown as means and SEM for three independent experiments.
Figure 5C:
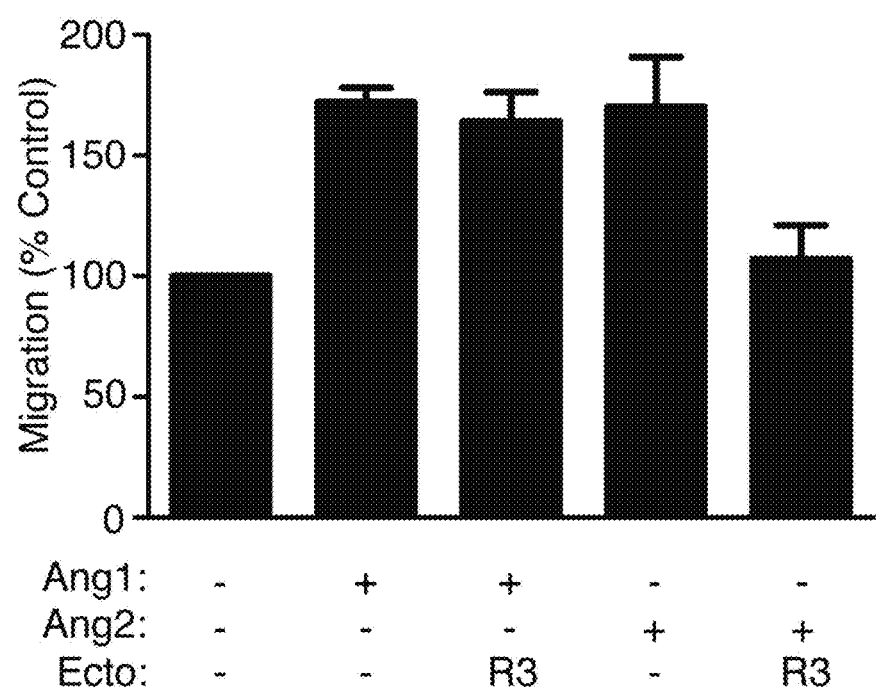
Figure 11:
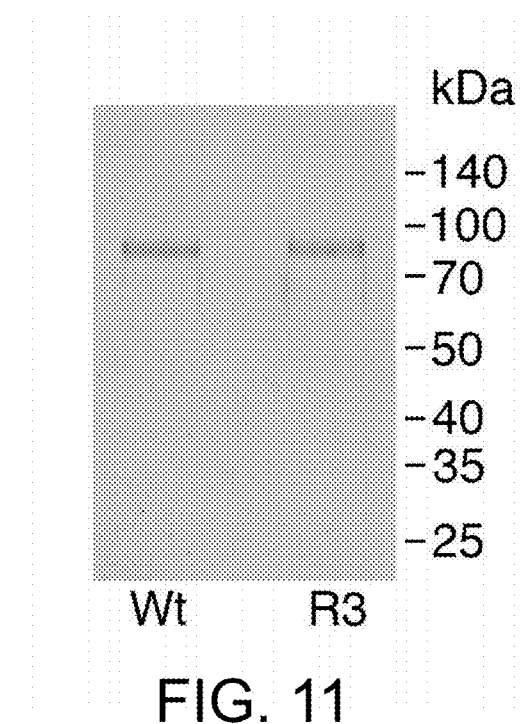
FIG. 11. Purified soluble ectodomain-Fc fusion proteins. Coomassie stained gel of wild type (Wt) and R3 ectodomain-Fc fusion proteins following expression in Hek 293 cells and purification on nickel columns. The positions of mass markers are indicated in kDa.

In order to analyse the binding characteristics of the evolved ectodomain in more detail we constructed the wild-type ectodomain (residues 1-442) with a carboxy-terminal Fc-tag and introduced the F161I and ΔR167, 1168 into this sequence by site directed mutagenesis. Wild-type and R3 ectodomains were expressed in HEK293 cells as secreted soluble proteins of approximately 80 kDa and purified (FIG. 11). Binding of Ang1 and Ang2 was examined using surface plasmon resonance. As expected the wild-type ectodomain bound both ligands (FIG. 4A). In contrast, the evolved ectodomain was only able to bind Ang2 and showed negligible Ang1 binding (FIG. 4A), consistent with our observation on this variant ectodomain when expressed on the cell surface (FIG. 2B). The affinity of interaction between Ang2 and the evolved ectodomain ($K_d$=2.4+/−0.3 nM) was similar to that with wild-type ectodomain (4.1+/−0.8 nM (n=3)). Maximal Ang2 binding was lower ($B_{max}$=0.25+/−0.02 arbitrary units) than with wild-type ($B_{max}$=0.67+/−0.06 arbitrary units (n=3)). It was surprising to us that changes at only three residues caused such a dramatic switch in the binding specificity of the receptor ectodomain. Loss of two residues and the conservative substitution of I for F are very unlikely to change the immunogenicity of this protein suggesting the evolved form will be well tolerated by the immune system if used therapeutically.

We were interested to examine the individual effects of the F161I substitution and double ΔR167,H168 deletion on binding. We therefore constructed wild-type Fc soluble ectodomain with F161I substitution or ΔR167,H168 changes and tested Ang1 and Ang2 binding in ELISA assays. There was no distinguishable difference between wild-type and F161I-ectodomains in binding to Ang1 (FIG. 4C). Similarly, Wild-type and F161I-ectodomains both bound equally well to Ang2 (FIG. 4C). In contrast, deletion of R167/H168 completely abolished ectodomain binding to Ang1 and Ang2

(FIG. 4C). This was an unexpected result and showed that the changes introduced by the directed evolution act in a uniquely combinatorial rather than an additive way to switch the binding specificity of the ectodomain.

The crystal structure of Tie2 ectodomain bound to Ang2 shows that F161 of Tie2 stacks with F469 in Ang2 (26). The equivalent position in Ang1 has a G residue rather than F. Substitution of I for F161 retains the hydrophobic character of this position but would negatively affect the aromatic stacking between F161 in Tie2 and F469 in Ang2. R167 in Tie2 appears to make a salt bridge with D448 in Ang2. As D448, and surrounding sequence, is conserved between Ang2 and Ang1 it would be anticipated that loss of R167 would affect binding to both ligands similarly. In the ectodomain H168 forms hydrogen bonds in Ang2 with S417 and Y476 and also interacts with P452 (26). In Ang1 S417 is an I whereas Y476 and P452 are conserved. However, loss of both R167 and H168 might be expected to significantly disrupt or alter the nature of the interface between Ang1/2 and Tie2.

To test the effects of R3 ectodomain on the cellular actions of Ang2 we examined its ability to interfere with Ang2 antagonism of Ang1 in the endothelial cell line EA.hy926. Endothelial cells challenged with Ang1 showed an activation of Akt and, consistent with the reported antagonist effects of Ang2, this was suppressed by Ang2 (FIG. 5A). Inclusion of wild-type ectodomain with Ang1 plus Ang2 further suppressed Akt activation, as expected from the ability of this fusion protein to bind Ang1 as well as Ang2. However, when the evolved ectodomain was added with Ang1 and Ang2 the inhibitory effect of Ang2 was reversed and Akt activation restored (FIG. 5A). To further examine the effects of evolved ectodomain we tested its effects on the agonist activity of Ang2. High concentrations of Ang2 have previously been reported to stimulate signalling in endothelial cells (27) and as shown in FIG. 5B, 1 μg/ml Ang2 caused a low level stimulation of Akt phosphorylation in EA.hy926 cells. However, whereas the stimulatory effect of Ang1 was unaffected by inclusion of the evolved ectodomain, the agonist activity of Ang2 was blocked (FIG. 5B). As an additional test of the ability of evolved ectodomain to inhibit Ang2 we examined the agonist activity of high Ang2 concentrations on migration of endothelial cells. Both Ang1 at 50 ng/ml and Ang2 at 1 μg/ml stimulated endothelial cell migration (FIG. 5C). Addition of the evolved ectodomain did not affect Ang1-induced migration but blocked migration in response to Ang2 (FIG. 5C).

Combining surface display with SHM-driven diversification has allowed us to evolve a new form of Tie2 ectodomain with dramatically shifted binding specificity and ability to sequester Ang2, a ligand associated with a range of pathologies. Soluble forms of this ectodomain bind Ang2 preventing it from antagonising Ang1, as well as inhibiting the agonist activity associated with high concentrations of Ang2. In contrast to Ang2, Ang1 has important roles in vascular protection so a molecule that can block Ang2 without interfering with Ang1 has significant benefits for therapeutic use, particularly in conditions associated with inflammation.

REFERENCES

1. Augustin H G, Young Koh G, Thurston G, Alitalo K (2009) Control of vascular morphogenesis and homeostasis through the angiopoietin-Tie system. *Nat Rev Mol Cell Biol* 10:165-177.
2. Huang H, Bhat A, Woodnutt G, Lappe R (2010) Targeting the ANGPT-TIE2 pathway in malignancy. *Nat Rev Cancer* 10:575-585.
3. Maisonpierre P C et al. (1997) Angiopoietin-2, a natural antagonist for Tie2 that disrupts in vivo angiogenesis. *Science* 277:55-60.
4. De Palma M et al. (2005) Tie2 identifies a hematopoietic lineage of proangiogenic monocytes required for tumor vessel formation and a mesenchymal population of pericyte progenitors. *Cancer Cell* 8:211-26.
5. Brindle N P J, Saharinen P, Alitalo K (2006) Signaling and Functions of Angiopoietin-1 in Vascular Protection. *Circ Res* 98:1014-1023.
6. Felcht M et al. (2012) Angiopoietin-2 differentially regulates angiogenesis through TIE2 and integrin signaling. *J Clin Invest* 122:1991-2005.
7. Mazzieri R et al. (2011) Targeting the ANG2/TIE2 Axis Inhibits Tumor Growth and Metastasis by Impairing Angiogenesis and Disabling Rebounds of Proangiogenic Myeloid Cells. *Cancer Cell* 19:512-526.
8. Welford A F et al. (2011) TIE2-expressing macrophages limit the therapeutic efficacy of the vascular-disrupting agent combretastatin A4 phosphate in mice. *J Clin Invest* 121:1969-73.
9. White R R et al. (2003) Inhibition of rat corneal angiogenesis by a nuclease-resistant RNA aptamer specific for angiopoietin-2. *Proc Natl Acad Sci USA* 100:5028-5033.
10. Oliner J et al. (2004) Suppression of angiogenesis and tumor growth by selective inhibition of angiopoietin-2. *Cancer Cell* 6:507-16.
11. Koh Y J et al. (2010) Double Antiangiogenic Protein, DAAP, Targeting VEGF-A and Angiopoietins in Tumor Angiogenesis, Metastasis, and Vascular Leakage. *Cancer Cell* 18:171-184.
12. Holopainen T et al. (2012) Effects of Angiopoietin-2-Blocking Antibody on Endothelial Cell—Cell Junctions and Lung Metastasis. *J Natl Cancer Inst* 104:461-475.
13. Tabruyn S P et al. (2010) Angiopoietin-2-Driven Vascular Remodeling in Airway Inflammation. *Am J Pathol* 177:3233-3244.
14. Economides A N et al. (2003) Cytokine traps: multi-component, high-affinity blockers of cytokine action. *Nat Med* 9:47-52.
15. Huang C (2009) Receptor-Fc fusion therapeutics, traps, and MIMETIBODY™ technology. *Curr Opin Biotech* 20:692-699.
16. Davis S et al. (1996) Isolation of angiopoietin-1, a ligand for the TIE2 receptor, by secretion-trap expression cloning. *Cell* 87:1161-9.
17. Yuan H T, Khankin E V, Karumanchi S A, Parikh S M (2009) Angiopoietin 2 Is a Partial Agonist/Antagonist of Tie2 Signaling in the Endothelium. *Mol Cell Biol* 29:2011-2022.
18. Jacket C, Kast P, Hilvert D (2008) Protein Design by Directed Evolution. *Annu Rev Biophys* 37:153-173.
19. Tracewell C A, Arnold F H (2009) Directed enzyme evolution: climbing fitness peaks one amino acid at a time. *Curr Opin Chem Biol* 13:3-9.
20. Sale J E, Calandrini D M, Takata M, Takeda S, Neuberger M S (2001) Ablation of XRCC2/3 transforms immunoglobulin V gene conversion into somatic hypermutation. *Nature* 412:921-926.
21. Cumbers S J et al. (2002) Generation and iterative affinity maturation of antibodies in vitro using hypermutating B-cell lines. *Nat Biotech* 20:1129-1134.

22. Wang L, Jackson W C, Steinbach P A, Tsien R Y (2004) Evolution of new nonantibody proteins via iterative somatic hypermutation. *Proc Natl Acad Sci USA* 101: 16745-16749.
23. Arakawa H et al. (2008) Protein evolution by hypermutation and selection in the B cell line DT40. *Nucleic Acids Res* 36:e1.
24. Macdonald P R et al. (2006) Structure of the extracellular domain of Tie receptor tyrosine kinases and localization of the angiopoietin-binding epitope. *J Biol Chem* 281:28408-28414.
25. Daugherty P S, Chen G, Iverson B L, Georgiou G (2000) Quantitative analysis of the effect of the mutation frequency on the affinity maturation of single chain Fv antibodies. *Proc Nati Acad Sci USA* 97:2029-2034.
26. Barton W A et al. (2006) Crystal structures of the Tie2 receptor ectodomain and the angiopoietin-2-Tie2 complex. *Nat Struct Mol Biol* 13:524-532.
27. Kim I et al. (2000) Angiopoietin-2 at high concentration can enhance endothelial cell survival through the phosphatidylinositol 3'-kinase/Akt signal transduction pathway. *Oncogene* 19:4549-4552.
28. Watson P J, Fairall L, Santos G M, Schwabe J W R (2012) Structure of HDAC3 bound to co-repressor and inositol tetraphosphate. *Nature* 481:335-340.

Example 2

In Vivo Activity of the Ang2 Ligand Trap R3

Figure 13:
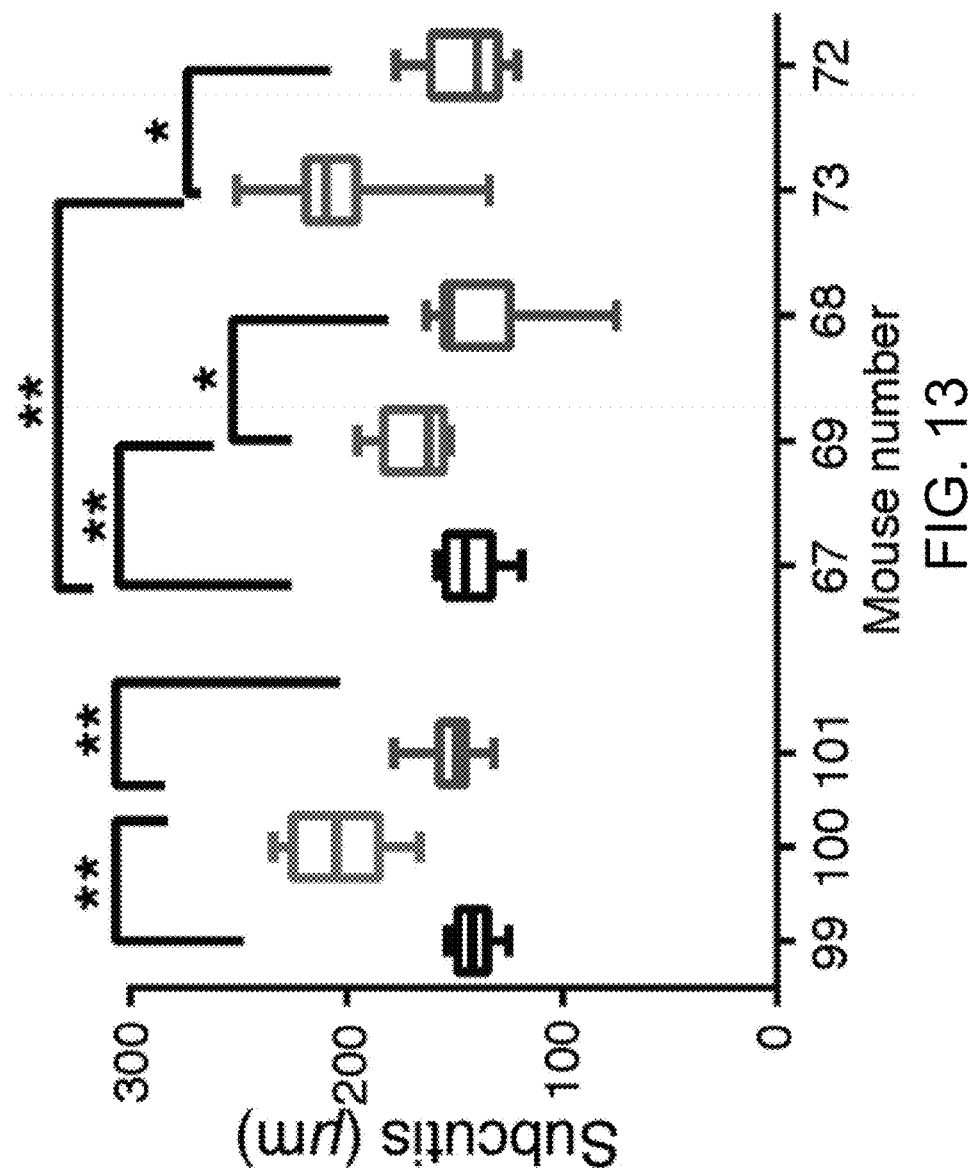
FIG. 13. Evolved ectodomain suppresses localized oedema in vivo. Quantitative analysis of local oedema formation in mice injected with control carrier (black), LPS, LPS with R3 ectodomain or LPS with inactive ΔR167,H168 ectodomain. Data from individual mouse hocks taken two hours post-injection are presented as mean subcutis thickness (distance between tibial periost and epidermis), minimum and maximum values +/−SD and compared to the matched controls for a minimum of nine data points (*P<0.005; **P<0.0001, Students 't' test). The experiment was performed at two independent times (mice 99-101 and 67-69, 72, 73) with the same stock of LPS.
Figure 14:
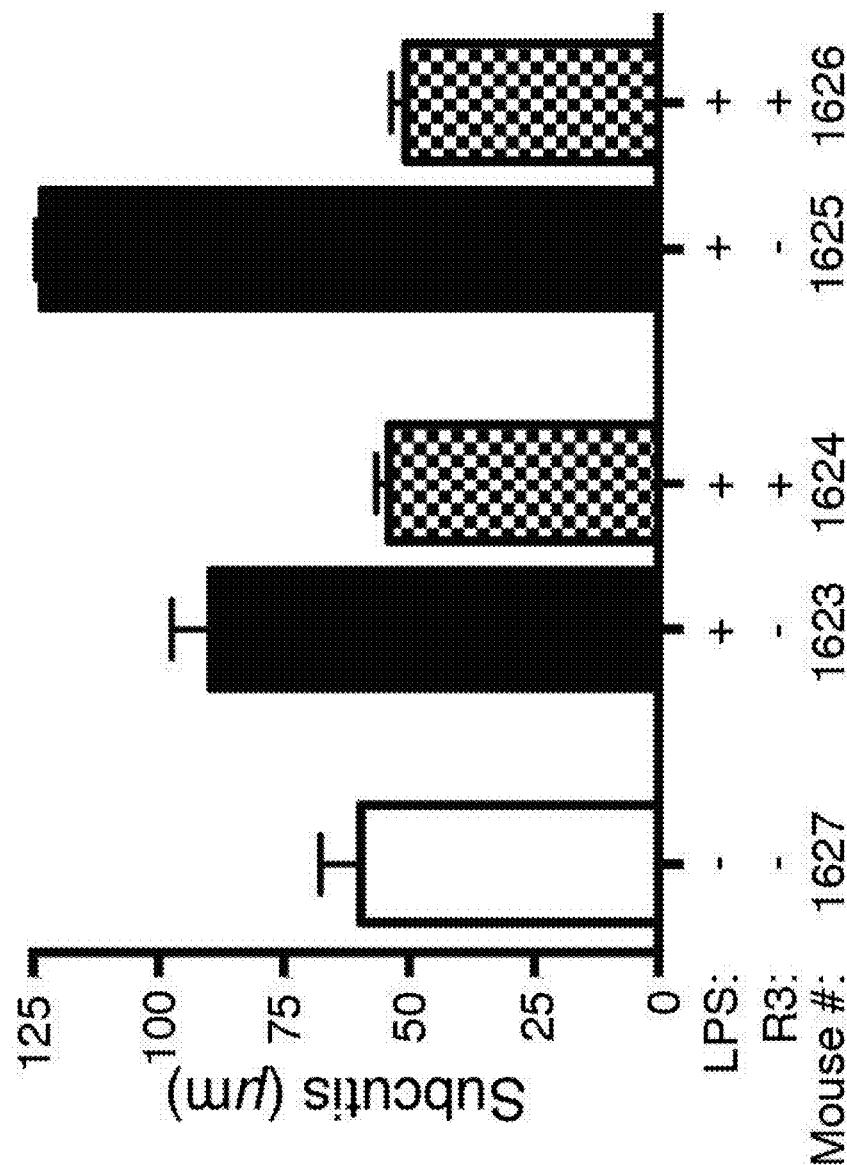
FIG. 14. Evolved ectodomain suppresses localized oedema in vivo. Quantitative analysis of local oedema formation in mice injected with control carrier, LPS or LPS with R3 ectodomain, as indicated. Data from individual mouse hocks taken one hour post-injection are presented as mean subcutis thickness and SD for four data points per mouse. Data are shown for each matched pair of mice.

The angiopoietins have key roles in regulating vascular inflammation and permeability (1, 2). Elevated Ang2 has been implicated in inflammation and oedema associated with a range of conditions including sepsis, adult respiratory distress syndrome and renal failure with multiorgan dysfunction (3-5). Ang2 stimulates local inflammatory responses characterized by vascular leakage (6) and is an essential mediator of vascular inflammation and oedema induced by pro-inflammatory cytokines and other stimuli, including lipopolysaccharide (LPS) (7, 8). To test the activity of the evolved ectodomain in vivo, therefore, we examined the ability of the protein to inhibit localized oedema formation induced by LPS in mice Animals were injected subcutaneously in the hock with control vehicle, LPS, LPS together with evolved ectodomain (R3) or LPS with the non-binding ΔR167,H168 ectodomain. As shown in FIG. 13, two hours post-injection LPS produced subcutaneous oedema as measured by subcutis thickness. However, when administered together with the evolved ectodomain this effect was blocked, consistent with the ability of the ectodomain to bind and block Ang2-mediated vascular permeability. In contrast, the ΔR167,H168 non-binding ectodomain failed to inhibit LPS-induced oedema. A similar experiment was performed to examine localized oedema one hour after LPS injection into hocks. Again, the evolved ectodomain (R3) blocked the ability of LPS to induce localized oedema associated with inflammation (FIG. 14).

Methods

Littermate C57Bl/6 mice (age and sex matched) were taken from colonies bred in a specific pathogen barrier unit at University of Leicester. Mice were humanely restrained, and received 5 μg LPS (*E. coli* 0111:B4, TLR grade; Enzo Life Sciences, Inc) with or without 15 μg purified evolved ectodomain or control ectodomain protein (in 10 μl volumes diluted in PBS). The injection site was the mouse hock. The procedure was compliant with Home Office regulations and institutional guidelines. At different times after injection mice were culled by cervical dislocation and hocks were prepared for histological analysis (fixation, decalcification using 6% (v/v) trichloroacetic acid in neutral buffered saline, and paraffin embedding). 5 μm sections were stained with Wright's stain and those selected in which the distance of the tibia periost to epidermis could be comparatively measured (using Delta Pix InSight (v.3.3.1) imaging software), providing a value of subcutis thickness (local oedema). Nine to 13 data points were obtained from each section, blinded for treatment. Statistical analysis was performed by unpaired 't' test of paired data sets, and $p<0.05$ considered significant.

REFERENCES

1. Augustin, H. G., Young Koh, G., Thurston, G., and Alitalo, K. (2009) Control of vascular morphogenesis and homeostasis through the angiopoietin-tie system. *Nat. Rev. Mol. Cell. Biol.* 10, 165-177
2. Brindle, N. P. J., Saharinen, P., and Alitalo, K. (2006) Signaling and functions of angiopoietin-1 in vascular protection. *Circ. Res.* 98, 1014-1023
3. Parikh, S M., Mammoto, T., Schultz, A., Yuan, H. T., Christiani, D., Karumanchi, S. A., and Sukhatme, V. P. (2006) Excess circulating angiopoietin-2 may contribute to pulmonary vascular leak in sepsis in humans. *PLoS Med.* 3
4. Alves, B., Montalvao, S., Aranha, F., Siegl, T., Souza, C., Lorand-Metze, I., Annichino-Bizzacchi, J., and De Paula, E. (2010) Imbalances in serum angiopoietin concentrations are early predictors of septic shock development in patients with post chemotherapy febrile neutropenia. *BMC Infect. Dis.* 10, 143
5. Kümpers, P., Hafer, C., David, S., Hecker, H., Lukasz, A., Fliser, D., Haller, H., Kielstein, J., and Faulhaber-Walter, R. (2010) Angiopoietin-2 in patients requiring renal replacement therapy in the icu: Relation to acute kidney injury, multiple organ dysfunction syndrome and outcome. *Intensive Care Med.* 36, 462-470
6. Roviezzo, F., Tsigkos, S., Kotanidou, A., Bucci, M., Brancaleone, V., Cirino, G., and Papapetropoulos, A. (2005) Angiopoietin-2 causes inflammation in vivo by promoting vascular leakage. *J. Pharmacol. Exp. Ther.* 314, 738-744
7. Fiedler, U., Reiss, Y., Scharpfenecker, M., Grunow, V., Thurston, G., Gale, N. W., Sobke, A., Herrmann, M., Preissner, K. T., Vajkoczy, P., and Augustin, H. G. (2005) Angiopoietin-2 sensitizes endothelial cells to tnf-alpha and is required for induction of inflammation. *Nat. Med.* 12, 235-239
8. Ziegler, T., Horstkotte, J., Schwab, C., Pfetsch, V., Weinmann, K., Dietzel, S., Rohwedder, I., Hinkel, R., Gross, L., Lee, S., Hu, J., Soehnlein, O., Franz, W. M., Sperandio, M., Pohl, U., Thomas, M., Weber, C., Augustin, H. G., Fassler, R., Deutsch, U., and Kupatt, C. (2013) Angiopoietin 2 mediates microvascular and hemodynamic alterations in sepsis. *J. Clin. Invest.* 123, 3436-3445

Example 3

Improved Ang2 Ligand-Trap

Figure 15A:
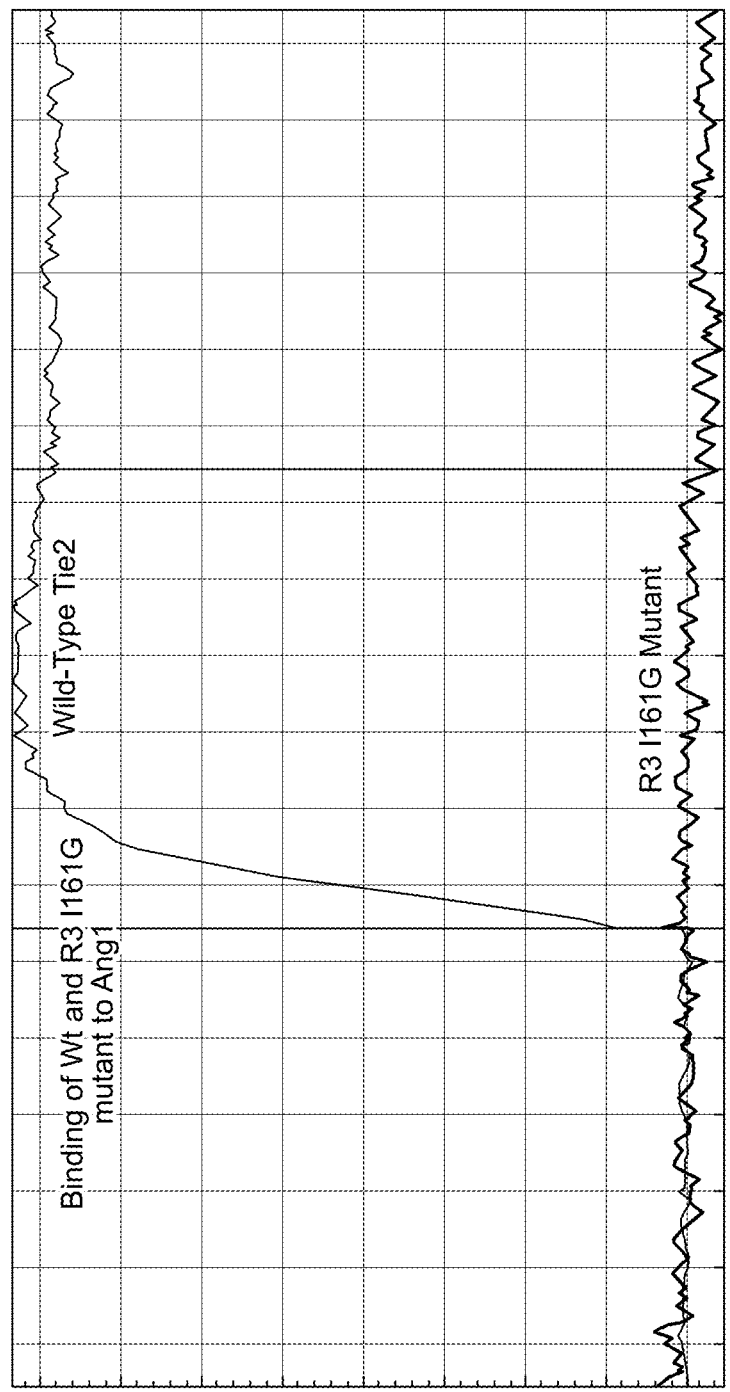
FIGS. 15A-B. SPR analysis of R3 I161G mutant binding showing the mutant does not bind Ang1 but shows increased Ang2 binding compared with R3.
Figure 15B:
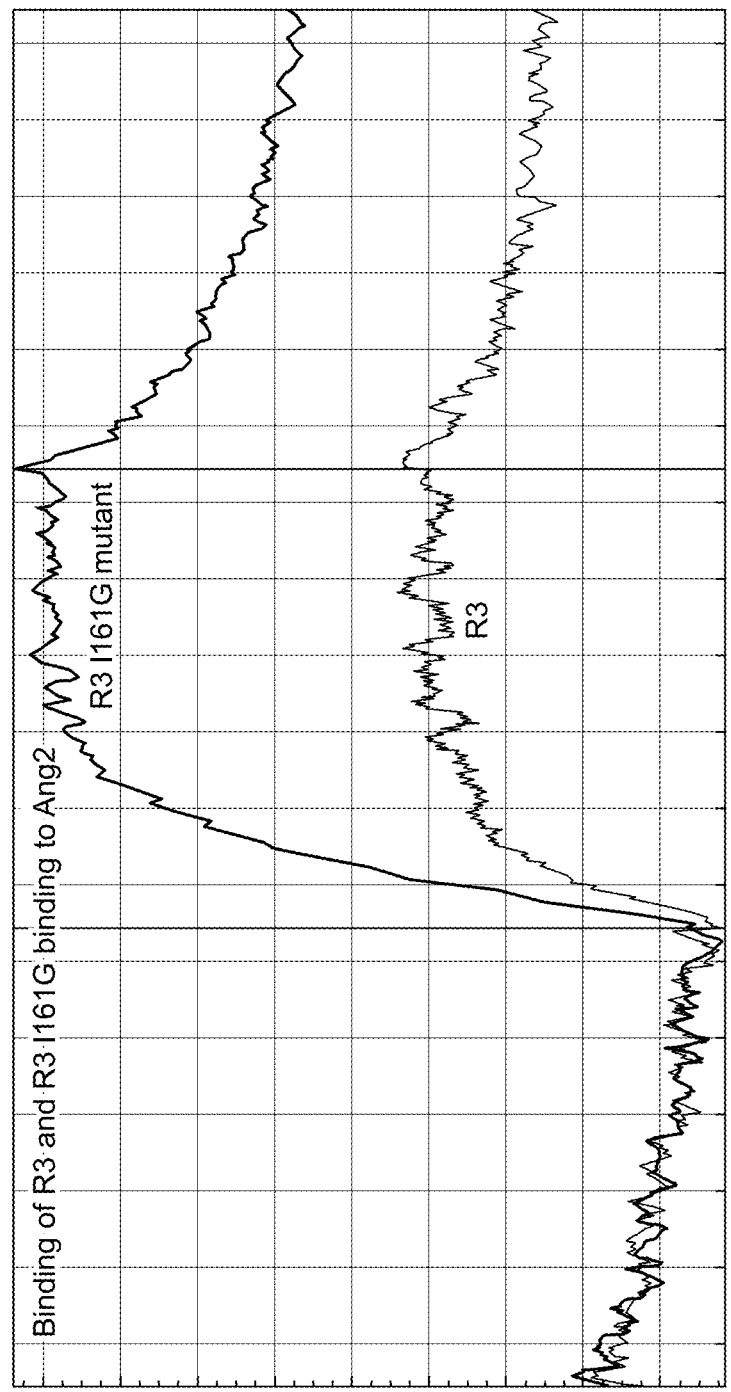
Figure 16:
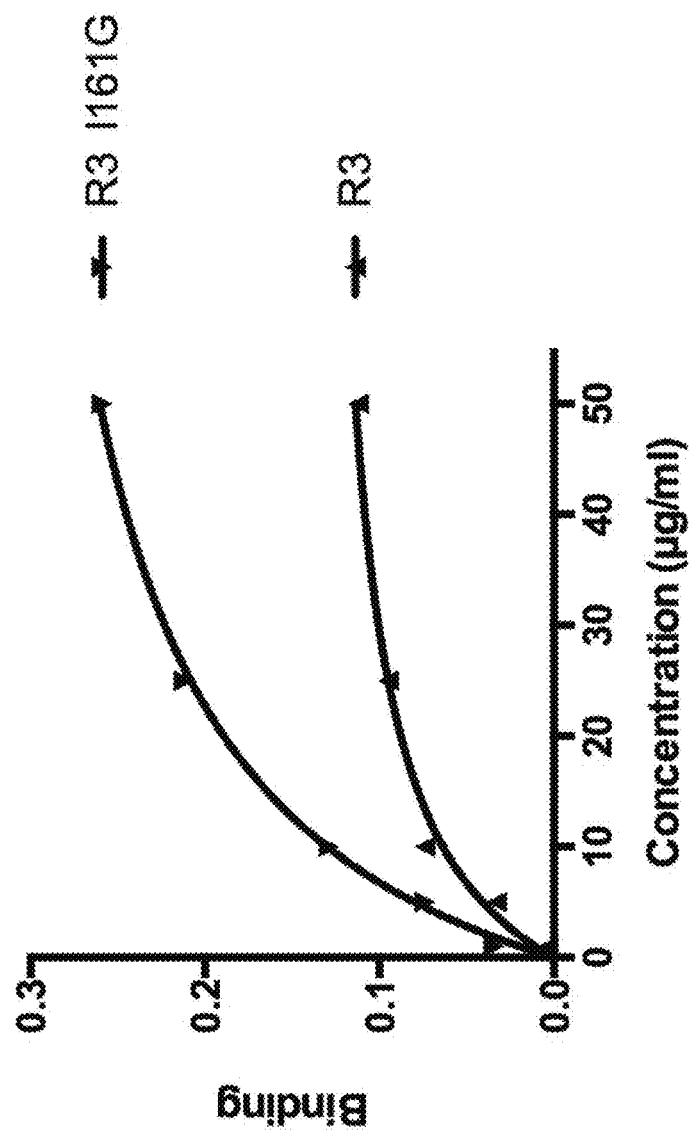
FIG. 16. Elisa binding of R3 and R3 I161 G mutant to immobilised Ang2 shows R3 I161 G mutant has improved Ang2 binding.

Using the insight provided by our evolved Tie2 ectodomain (designated R3) we have generated an additional mutant which may have improved Ang2 binding. We generated the new mutant by analysing the possible mechanisms by which the evolved Ang2-specific ligand trap (deletion of R167/H168 and substitution of I161 for F) displays Ang2 specific binding. Essentially this involved determining possible hydrogen bonding, salt bridges, electrostatic and hydrophobic interactions that could contribute to specific Ang2 binding in the evolved ectodomain by computationally visualising the published wild-type structure but with the changes we created in the evolved ectodomain (R3). This led us to hypothesise that a smaller residue at position 161 could further increase Ang2 binding without increasing Ang1 binding. This mutant (deleted at R167 and 11168 and with Glycine at 161) was created, expressed and assayed for binding by SPR (FIG. 15). The new mutant showed specific binding to Ang2 over Ang1 (as did the evolved R3 protein), and a higher level of binding to Ang2 than the original evolved ectodomain displayed. This new mutant is a development of our original R3 Ang2-specific ligand trap. The binding to Ang2 was also analysed by ELISA, again showing increased Ang2 binding (FIG. 16).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A polypeptide comprising a modified angiopoietin receptor or fragment thereof, wherein the fragment comprises a sequence corresponding to residues 23-210 of SEQ ID NO: 1, wherein the polypeptide binds preferentially to angiopoietin-2 (Ang2) compared to angiopoeitin-1 (Ang1); wherein the angiopoietin receptor is Tie2, and wherein the polypeptide comprises the following mutations with respect to SEQ ID NO: 1 or SEQ ID NO: 2:
   (i) F161I, ΔR167 and ΔH168, or
   (ii) F161G, ΔR167 and ΔH168.

2. A polypeptide according to claim 1, wherein the polypeptide binds to Ang2 and Ang1 with an affinity ratio of at least 10:1.

3. A polypeptide according to claim 1, wherein the polypeptide binds to Ang2 with a $K_d$ of less than 10 nM and/or the polypeptide binds to Ang1 with a $K_d$ of greater than 1 μM.

4. A composition comprising a polypeptide according to claim 1 and a pharmaceutically acceptable carrier, diluent or excipient.

5. A polypeptide according to claim 1, wherein the polypeptide comprises the amino acid sequence of SEQ ID NO: 3.

6. A polypeptide that binds preferentially to angiopoietin-2 compared to angiopoietin-1, said polypeptide comprising the amino acid sequence of SEQ ID NO: 3.

* * * * *